US011392117B2

(12) United States Patent
Pal et al.

(10) Patent No.: US 11,392,117 B2
(45) Date of Patent: Jul. 19, 2022

(54) METHOD AND DEVICE FOR MANAGING INTERACTION BETWEEN A WEARABLE DEVICE AND A VEHICLE

(71) Applicant: SONY CORPORATION, Tokyo (JP)

(72) Inventors: Pralay Kumar Pal, Bangalore (IN); Pramod Chintalapoodi, San Diego, CA (US); Sho Tanaka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 9 days.

(21) Appl. No.: 15/047,463

(22) Filed: Feb. 18, 2016

(65) Prior Publication Data
US 2017/0242428 A1   Aug. 24, 2017

(51) Int. Cl.
*H04W 12/00* (2021.01)
*G05D 1/00* (2006.01)
(Continued)

(52) U.S. Cl.
CPC .............. *G05D 1/0016* (2013.01); *A61B 5/01* (2013.01); *A61B 5/021* (2013.01); *A61B 5/024* (2013.01);
(Continued)

(58) Field of Classification Search
CPC ..... H04W 12/00; H04W 12/02; H04W 12/04; H04W 12/06; H04W 12/08; H04W 12/10; H04W 12/12; H04W 76/02; H04W 76/021; G08B 21/02; G08B 21/0297; G08B 21/04; G08B 21/06; G08B 13/19647;
(Continued)

(56) References Cited

U.S. PATENT DOCUMENTS

| 5,513,107 A * | 4/1996 | Gormley ............ B60G 17/0195 180/287 |
| 9,439,082 B2 * | 9/2016 | Fischer ................... H04M 3/28 |

(Continued)

FOREIGN PATENT DOCUMENTS

| CN | 104627091 A | 5/2015 |
| CN | 104875746 A | 9/2015 |

(Continued)

OTHER PUBLICATIONS

TECHMAHINDRALIMITED, "Project S3O Tech Mahindra Project ID: C01000000017417", Sony, Document ID: S3O_003 Rev. 0, 2015, pp. 10.

(Continued)

*Primary Examiner* — Richard A Goldman
(74) *Attorney, Agent, or Firm* — Chip Law Group

(57) ABSTRACT

Various aspects of a device and method to manage interaction with one or more control circuits in a vehicle and one or more wearable devices are disclosed herein. The device comprises one or more circuits configured to receive a first set of input values from the one or more wearable devices associated with a first user. The one or more wearable devices are communicatively coupled to the device used in the vehicle. A second set of input values is received from one or more vehicle sensors embedded in the vehicle. An operating mode of the device is determined based on the received first set of input values and the second set of input values. One or more functions of the vehicle are controlled based on the determined operating mode of the device.

22 Claims, 13 Drawing Sheets

(51) Int. Cl.

| | |
|---|---|
| *B60K 37/06* | (2006.01) |
| *B60K 28/06* | (2006.01) |
| *B60K 28/10* | (2006.01) |
| *A61B 5/318* | (2021.01) |
| *H04W 4/90* | (2018.01) |
| *H04W 4/80* | (2018.01) |
| *A61B 5/01* | (2006.01) |
| *A61B 5/021* | (2006.01) |
| *A61B 5/024* | (2006.01) |
| *A61B 5/08* | (2006.01) |
| *A61B 5/145* | (2006.01) |
| *A61B 5/00* | (2006.01) |
| *B60H 1/00* | (2006.01) |
| *B60R 16/03* | (2006.01) |
| *B60R 25/10* | (2013.01) |
| *G01C 21/34* | (2006.01) |
| *G05D 1/02* | (2020.01) |
| *H04W 84/12* | (2009.01) |

(52) U.S. Cl.
CPC ........ *A61B 5/0816* (2013.01); *A61B 5/14542* (2013.01); *A61B 5/318* (2021.01); *A61B 5/6801* (2013.01); *A61B 5/7282* (2013.01); *B60H 1/00742* (2013.01); *B60K 28/06* (2013.01); *B60K 28/063* (2013.01); *B60K 28/10* (2013.01); *B60K 37/06* (2013.01); *B60R 16/03* (2013.01); *B60R 25/10* (2013.01); *G01C 21/34* (2013.01); *G05D 1/0212* (2013.01); *H04W 4/80* (2018.02); *H04W 4/90* (2018.02); *B60K 2370/122* (2019.05); *B60K 2370/1438* (2019.05); *B60K 2370/167* (2019.05); *B60K 2370/175* (2019.05); *B60K 2370/178* (2019.05); *B60K 2370/48* (2019.05); *B60K 2370/55* (2019.05); *B60K 2370/573* (2019.05); *B60K 2370/58* (2019.05); *B60K 2370/583* (2019.05); *B60K 2370/589* (2019.05); *B60K 2370/5899* (2019.05); *B60K 2370/592* (2019.05); *B60K 2370/595* (2019.05); *B60K 2370/5911* (2019.05); *B60K 2370/62* (2019.05); *B60K 2370/73* (2019.05); *B60K 2370/741* (2019.05); *B60W 2540/043* (2020.02); *G05D 2201/0212* (2013.01); *H04W 84/12* (2013.01)

(58) Field of Classification Search
CPC ..... G08B 25/016; B60W 40/09; B60W 10/04; B60W 10/18; B60W 10/20; B60W 10/22; B60W 2040/0809; B60W 2040/0818; B60W 2540/18; B60W 2540/24; B60W 2540/26; B60W 2540/28; B60R 16/037; G06F 21/31; G06F 21/32; B06F 3/017
USPC .............. 701/41, 2, 23, 36, 45, 48; 340/5.8; 180/287
See application file for complete search history.

(56) References Cited

U.S. PATENT DOCUMENTS

| | | | | |
|---|---|---|---|---|
| 9,481,326 | B2* | 11/2016 | Chatterjee | B60H 1/00642 |
| 9,571,955 | B1* | 2/2017 | Mohdi | H04W 8/005 |
| 10,846,633 | B2* | 11/2020 | Magazinik | G06Q 50/32 |
| 2003/0076968 | A1* | 4/2003 | Rast | H04B 1/082 |
| | | | | 381/124 |
| 2007/0276944 | A1* | 11/2007 | Samovar | G07C 9/27 |
| | | | | 709/225 |
| 2008/0174451 | A1* | 7/2008 | Harrington | G08B 21/06 |
| | | | | 340/905 |
| 2012/0212353 | A1* | 8/2012 | Fung | B60W 30/02 |
| | | | | 340/905 |
| 2012/0320891 | A1* | 12/2012 | Moeller | H04W 4/027 |
| | | | | 370/338 |
| 2013/0226371 | A1* | 8/2013 | Rovik | H04L 63/102 |
| | | | | 701/2 |
| 2014/0240086 | A1* | 8/2014 | Van Wiemeersch | G05B 1/00 |
| | | | | 340/5.51 |
| 2014/0277894 | A1* | 9/2014 | Doyle | B60W 10/26 |
| | | | | 701/23 |
| 2014/0306799 | A1* | 10/2014 | Ricci | H04W 4/21 |
| | | | | 340/5.83 |
| 2014/0306826 | A1* | 10/2014 | Ricci | G09G 5/37 |
| | | | | 340/573.1 |
| 2014/0309849 | A1* | 10/2014 | Ricci | G01C 21/26 |
| | | | | 701/33.4 |
| 2015/0081169 | A1 | 3/2015 | Pisz | |
| 2015/0127215 | A1* | 5/2015 | Chatterjee | B60R 16/037 |
| | | | | 701/36 |
| 2015/0149018 | A1* | 5/2015 | Attard | G05D 1/0061 |
| | | | | 701/23 |
| 2016/0039424 | A1 | 2/2016 | Hong et al. | |
| 2016/0244023 | A1* | 8/2016 | Masucci | B60R 25/252 |
| 2017/0242428 | A1* | 8/2017 | Pal | A61B 5/021 |
| 2017/0316254 | A1* | 11/2017 | Hariri | G06K 9/00255 |
| 2018/0009416 | A1* | 1/2018 | Maiwand | G07C 9/00571 |
| 2020/0062269 | A1* | 2/2020 | Vardharajan | G07C 5/008 |
| 2020/0209894 | A1* | 7/2020 | Torii | B64D 47/02 |

FOREIGN PATENT DOCUMENTS

| | | | |
|---|---|---|---|
| CN | 104992391 A | | 10/2015 |
| CN | 105216624 A | | 1/2016 |
| DE | 102004059713 A1 | * | 12/2003 |
| JP | 2004046450 A | * | 10/2002 |
| WO | 2014171734 A1 | | 10/2014 |

OTHER PUBLICATIONS

Office Action for CN Patent Application No. 201780010384.7 dated Jan. 14, 2021, 12 pages of Office Action and 17 pages of English Translation.

* cited by examiner

METHOD AND DEVICE FOR MANAGING INTERACTION BETWEEN A WEARABLE DEVICE AND A VEHICLE

CROSS-REFERENCE TO RELATED APPLICATIONS/INCORPORATION BY REFERENCE

None.

FIELD

Various embodiments of the disclosure relate to a method and device to manage interaction between a wearable device and a vehicle. More specifically, various embodiments of the disclosure relate to a method and device to manage interaction with one or more wearable devices and one or more control circuits of a vehicle.

BACKGROUND

Currently, wearable technology and associated devices are one of the most burgeoning segments in the electronics industry. Wearable devices are increasingly used in the health domain to monitor health parameters, such as heart rate, pulse oximetry, respiratory rate, and/or blood pressure, of a user.

In certain scenarios, the wearable devices may also be used in wellness and fitness tracking of the user, such as a vehicle user, based on a measure of calorie intake, calories burned, sleep pattern, physical activity, and/or the like. However, the wearable devices worn by the user may be of limited use as interactions with the vehicle may not be performed in a convenient manner. There is a need for a smart mechanism that may interface between the wearable devices and the vehicle. Such a smart mechanism may maximize usability of the wearable devices, ensure safety of the vehicle user, and/or provide an enhanced user experience.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

A method and device to manage interaction between a wearable device and a vehicle substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
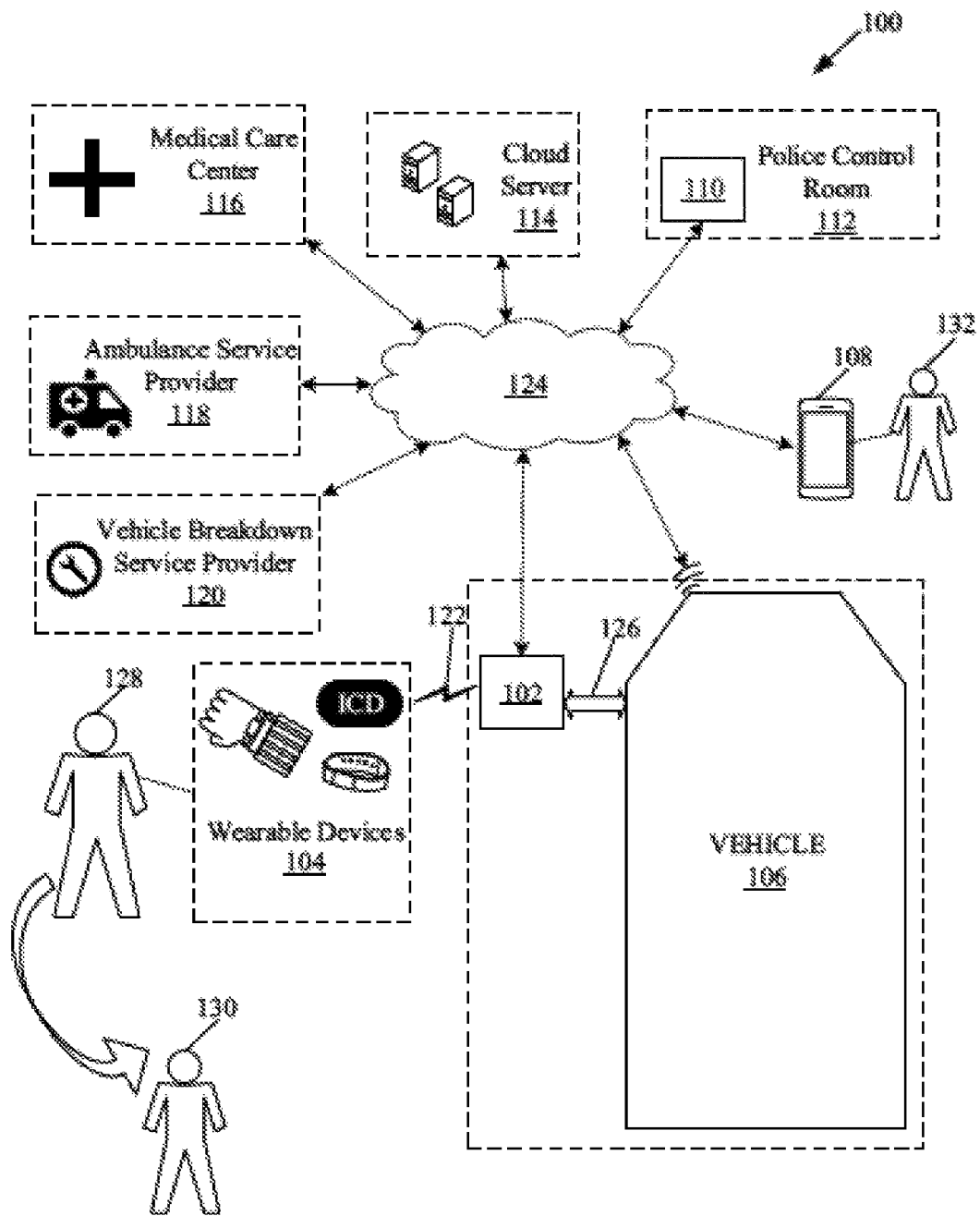
FIG. 1 is a block diagram that illustrates a network environment for a device that manages interaction with one or more control circuits in a vehicle and one or more wearable devices, in accordance with an embodiment of the disclosure.

The following described implementations may be found in the disclosed device and method used to manage interaction with one or more control circuits in a vehicle and one or more wearable devices. Exemplary aspects of the disclosure may comprise a method that may receive a first set of input values from one or more wearable devices communicatively coupled to a device, such as a gateway device, used in a vehicle. The one or more wearable devices may be associated with a first user. A second set of input values may be received from one or more vehicle sensors embedded in the vehicle. An operating mode of the device may be determined based on the received first set of input values and the second set of input values. One or more functions of the vehicle may be controlled based on the determined operating mode of the device.

In accordance with an embodiment, a data type of the received first set of input values and the second set of input values may be determined. The control of the one or more functions of the vehicle may be further based on the determined data type and one or more pre-configured user settings associated with the first user.

In accordance with an embodiment, a current location information of the vehicle, a motion status of the vehicle, and/or the determined data type may be utilized for the determination of the operating mode. The operating mode may correspond to a home mode, an about-to-drive mode, an outside driving mode, an outside non-driving mode, a vehicle-health mode, and a user-critical health mode.

In accordance with an embodiment, the one or more functions may include opening or closing of a vehicle door, control of vehicle ignition, and/or control of vehicle speed. The one or more functions may also include dynamic configuration of pre-defined personalization settings associated with the first user. The first user may be authenticated at the vehicle. Further, the one or more functions may include adjustment of vehicle internal ambience, adjustment of a vehicle seat, and/or adjustment of a position of a vehicle mirror. The one or more functions may further include synchronization of personal data collected from the one or more wearable devices with the device (such as the gateway device).

In accordance with an embodiment, the first user may be authenticated based on the first set of input values received from the one or more wearable devices communicatively coupled to the device used in the vehicle. A communication may be performed with the one or more wearable devices at a pre-defined time interval. The communication may be performed when the vehicle is in motion to confirm a presence of the authenticated first user. Further, the communication may be performed when the determined operating mode is an outside driving mode.

In accordance with an embodiment, a theft alert may be communicated to a communication device located within a vicinity of the vehicle. The theft alert may be communicated when the authenticated first user is not detected in the vehicle in the outside driving mode. In accordance with an embodiment, the authentication may be transferred to another device associated with a second user to signal the user to move the vehicle within a pre-defined time interval. The authentication may be transferred when the determined operating mode is an outside non-driving mode.

In accordance with an embodiment, an abnormal medical condition may be detected based on vital health data received from the one or more wearable devices or a portable electronic device associated with the first user. A severity level of the detected abnormal medical condition may be determined. In accordance with an embodiment, based on the determined severity level, the determined operating mode, and/or a pre-determined health threshold associated with the first user, the vehicle speed may be controlled. Further, a health alert notification with current location information of the first user may be sent to a mobile device of a caregiver, a hospital, and/or ambulance, and/or a guidance may be generated for the first user to reach the nearest hospital.

In accordance with an embodiment, instructions from the caregiver may be received for the control of the one or more functions of the vehicle when the determined operating mode is an outside driving mode. Steering of the vehicle may be automatically controlled to drive the vehicle to a medical care center in the vicinity of the vehicle. The steering may be automatically controlled when the vehicle is in an autonomous driving mode and when the determined operating mode is an outside driving mode.

In accordance with an embodiment, the temperature inside the vehicle may be controlled based on the current body temperature of the first user received from the one or more wearable devices. The temperature inside the vehicle may be controlled when the first user is outside the vehicle and when the determined operating mode is an outside non-driving mode or a home mode.

In accordance with an embodiment, a temperature change signal may be sent to an electronic control unit of the vehicle at pre-defined time intervals. The temperature change signal may be sent at pre-defined time intervals when the first user is detected inside the vehicle and when the determined operating mode is outside driving mode.

In accordance with an embodiment, information of alcohol intoxication level associated with the first user may be received from the one or more wearable devices when the determined operating mode is the outside non-driving mode or the outside driving mode.

FIG. 1 is a block diagram that illustrates a network environment for a device that manages interaction with one or more control circuits in a vehicle and one or more wearable devices, in accordance with an embodiment of the disclosure. With reference to FIG. 1, there is shown a network environment 100. The network environment 100 may include a device 102, one or more wearable devices 104, a vehicle 106, a mobile device 108, a communication device 110, a police control room 112, a cloud server 114, a medical care center 116, an ambulance service provider 118, a vehicle breakdown service provider 120, a first communication network 122, a second communication network 124, an in-vehicle network 126, and one or more users. The one or more users may include a first user 128, a second user 130, and a caregiver 132. The first user 128 may be an owner, a driver, and/or a user of the vehicle 106 and may be associated with the one or more wearable devices 104. The second user 130 may be a valet. The caregiver 132 may be associated with the mobile device 108.

The device 102 may be referred to as a gateway device that may be communicatively coupled to the one or more wearable devices 104, via the first communication network 122. The device 102 may be further communicatively coupled to one or more control circuits, such as an electronic control unit (ECU) in the vehicle 106, via the in-vehicle network 126. In accordance with an embodiment, the device 102 may also be communicatively coupled to one or more external devices, such as the mobile device 108, the communication device 110, the cloud server 114, the medical care center 116, the ambulance service provider 118, and the vehicle breakdown service provider 120, via the second communication network 124. In accordance with an embodiment, the device 102 may be used in the vehicle 106. The device 102 may act as a communication bridge among the one or more wearable devices 104, the one or more control circuits in the vehicle 106, and the one or more external devices.

The device 102 may comprise suitable logic, circuitry, interfaces, and/or code that may be configured to interface with various wearable devices and a vehicle infrastructure. The wearable devices may correspond to the one or more wearable devices 104 and the vehicle infrastructure may correspond to the one or more internal electronic control units (ECUs) of the vehicle 106. In other words, the device 102 may be referred to as a gateway device, which acts as a communication bridge between the one or more wearable devices 104 and the one or more control circuits, such as the ECUs, of the vehicle 106. In accordance with an embodiment, the device 102 may be configured to establish a communication channel with the external devices, via the second communication network 124, when a communication with the external devices could not be established by use of a wireless communication system of the vehicle 106.

The one or more wearable devices 104 may refer to wearable electronics and/or electronic implants. The one or more wearable devices 104 may comprise suitable logic, circuitry, interfaces, and/or code that may be configured to communicate a first set of input values to the device 102. The one or more wearable devices 104 may be worn by the first user 128, associated with the vehicle 106. The one or more wearable devices 104 may be used by the first user 128 for healthcare purpose or for wellness and fitness tracking purpose. For example, a smart-glass, a smart-band or a smart-watch worn by the first user 128 may be used to measure calorie intake, calories burned, sleep patterns, and/or physical activity of the first user 128. Examples of the one or more wearable devices 104 may include, but are not limited to, a nicotine patch, a motion sickness patch, an iontophoresis patch (that uses electrical current for transdermal delivery of a drug), a glucose monitor, a wearable cardiac-event recorder, a biocompatible sensor (that may be attached, worn, or implanted into to a human body to predict ovulation cycle, monitor health parameters, such as heart rate, pulse oximetry, respiratory rate, and/or blood pressure), an implantable radio frequency device, such as the, "Obamacare microchip RFID implant", used for patient identification and health information, for the reformation of the healthcare system in the United States of America (U.S.), and/or other such wearable or implantable medical device that may provide diagnostic and therapeutic options for various illnesses and medical conditions.

The vehicle 106 may comprise one or more control units, such as the ECUs, which may be configured to communicate with the device 102. The vehicle 106 may operate in an autonomous mode, a semi-autonomous mode, or a manual mode. Examples of vehicle 106 may include, but are not limited to, a motor vehicle, a hybrid vehicle, and/or a vehicle that uses one or more distinct renewable or non-renewable power sources. A vehicle that uses renewable or non-renewable power sources may include a fossil fuel-based vehicle, an electric propulsion-based vehicle, a hydrogen fuel-based vehicle, a solar-powered vehicle, and/or a vehicle powered by other forms of alternative energy sources.

The mobile device 108 may comprise suitable logic, circuitry, interfaces, and/or code that may be configured to communicate instructions from a user, such as the caregiver 132, in response to a request or health information received from the device 102. The instruction may be communicated to control one or more functions of the vehicle 106 or to guide the first user 128 when the first user 128 is in a critical heath condition. Examples of the mobile device 108 may include, but are not limited to, a smartphone, a tablet computer, a laptop, a smart-watch, and/or a personal computing device.

The communication device 110 may comprise suitable logic, circuitry, interfaces, and/or code that may be configured to receive one or more theft alerts from various vehicles, such as the vehicle 106, or from various subscribed devices, such as the device 102. In accordance with an embodiment, one or more communication devices, such as the communication device 110, may be situated at one or more police stations, such as the police control room 112.

The cloud server 114 may comprise suitable logic, circuitry, interfaces, and/or code that may be configured to receive heath data, such as vital physiological data, from the device 102 or the wireless communication system of the vehicle 106. The cloud server 114 may be configured to store the received heath data for later use during authentication of one or more users, such as the first user 128. The cloud server 114 may be a web server, a database server, a file server, an application server, or a combination thereof. The cloud server 114 may be implemented by use of several technologies that are well known to those skilled in the art.

The medical care center 116 may refer to a hospital or medical clinic that may have a facility, such as a server or a communication medium, to receive health alert notifications from pre-registered external devices or vehicles, such as the vehicle 106. When the health alert notifications are received, the medical care center 116 may route the health alert to suitable department, doctors, and/or other personnel to make arrangements or initiate preparation for the treatment of a patient, such as the first user 128.

The ambulance service provider 118 may refer to a service provider for an ambulance or other specialized vehicles equipped to handle various medical emergencies. Similar to the medical care center 116, the ambulance service provider 118 may have a facility, such as a server or a communication medium, to receive health alert notifications from external devices or vehicles, such as the vehicle 106. The ambulance service provider 118 may refer to an ambulance that may be equipped to communicate with various other vehicles, such as the vehicle 106, or subscribed devices, such as the device 102.

The vehicle breakdown service provider 120 may refer to a service provider that assists vehicle users during a mechanical or an electrical breakdown of a vehicle, such as the vehicle 106. The vehicle breakdown service provider 120 may have a facility, such as a server or a communication medium, to receive requests from one or more electronic devices, such as the device 102, for provision of emergency support when the vehicle 106 is immobilized at home or on a road.

The first communication network 122 may include a medium through which the one or more wearable devices 104 may communicate with the device 102. Examples of the first communication network 122 may include, but are not limited to, short range networks (such as a home network), a 2-way radio frequency network (such as a Bluetooth-based network), a Wireless Fidelity (Wi-Fi) network, a Wireless Personal Area Network (WPAN), and/or a Wireless Local Area Network (WLAN). Various wearable devices, such as the one or more wearable devices 104, may be operable to connect to the device 102, in the first communication network 122, in accordance with various wired or wireless communication protocols or interoperability standards related to health informatics. Examples of such wired or wireless communication protocols or technical standards may include, but are not limited to, International Organization for Standardization's (ISO) Technical Committee (TC) on health informatics (ISO/TC 215), ISO/IEEE-11073 personal health data (PHD) standards, technical standards of continua (associated with Continua Health Alliance), Health Level-7 (HL7) standards, ISO 27799, ISO 17115, ISO/TR 16056-1 and 2, ISO/TS 16058, Bluetooth protocol, an infrared protocol, a Wireless Fidelity (Wi-Fi) protocol, a ZigBee protocol, IEEE 802.11, 802.16, cellular communication protocols, a Near Field Communication (NFC) protocol, a Universal Serial Bus (USB) protocol, and/or a wireless USB protocol.

The second communication network 124 may include a wireless medium through which the device 102 may communicate with the one or more external devices, such as the mobile device 108, the communication device 110, the cloud server 114, the medical care center 116, the ambulance service provider 118, and/or the vehicle breakdown service provider 120. Examples of the second communication network 124 may include, but are not limited to, the Internet, a cloud network, a Local Area Network (LAN), a telephone line (POTS), a Metropolitan Area Network (MAN), a dedicated short-range communication (DSRC) network, a mobile ad-hoc network (MANET), a vehicular ad-hoc network (VANET), Intelligent vehicular ad-hoc network (InVANET), Internet based mobile ad-hoc networks (IMANET), a wireless sensor network (WSN), a wireless mesh network (WMN), a Wireless Local Area Network (WLAN), and/or a cellular network, such as a long-term evolution (LTE) 3G and/or 4G network. Various devices in the network environment 100 may be operable to connect to the second communication network 124, in accordance with various wireless communication protocols. Examples of such wireless communication protocols, communication standards, and technologies may include, but are not limited to, IEEE 802.11, 802.11p, 802.15, 802.16, 1609, Worldwide Interoperability for Microwave Access (Wi-MAX), Wireless Access in Vehicular Environments (WAVE), Transmission Control Protocol and Internet Protocol (TCP/IP), User Datagram Protocol (UDP), Hypertext Transfer Protocol (HTTP), Long-term Evolution (LTE), File Transfer Protocol (FTP), Enhanced Data GSM Environment (EDGE), voice over Internet Protocol (VoIP), a protocol for email, instant messaging, and/or Short Message Service (SMS), and/or cellular communication protocols.

The in-vehicle network 126 may include a medium through which the device 102 may communicate with the one or more control circuits, such as one or more internal ECUs or other control systems, of the vehicle 106. The device 102 may use various in-vehicle communication protocols, such as controller area network (CAN), Local Interconnect Network (LIN), Ethernet or other communication protocols of the in-vehicle network 126 for connectivity to the one or more control circuits of the vehicle 106. Various control units, devices, or control systems in the vehicle 106 may also be configured to connect to the in-vehicle network 126, in accordance with various wired and wireless communication protocols. Examples of the wired and wireless communication protocols for the in-vehicle network 126 may include, but are not limited to, a vehicle area network (VAN), a CAN bus, Domestic Digital Bus (D2B), Time-Triggered Protocol (TTP), FlexRay, IEEE 1394, Carrier Sense Multiple Access With Collision Detection (CSMA/CD) based data communication protocol, Inter-Integrated Circuit ($I^2C$), Inter Equipment Bus (IEBus), Society of Automotive Engineers (SAE) J1708, SAE J1939, International Organization for Standardization (ISO) 11992, ISO 11783, Media Oriented Systems Transport (MOST), MOST25, MOST50, MOST150, Plastic optical fiber (POF), Power-line communication (PLC), and/or Serial Peripheral Interface (SPI) bus.

In operation, the device 102 may be configured to receive a first set of input values from the one or more wearable devices 104. The one or more wearable devices 104 may be communicatively coupled to the device 102 (used in the vehicle 106), via the first communication network 122. The one or more wearable devices 104 may be worn by the first user 128. In accordance with an example, the one or more wearable devices 104 may be a smart-glass, a smart-band or a smart-watch worn by the first user 128. The device 102 may be configured to receive a second set of input values from the one or more vehicle sensors embedded in the vehicle 106, via the in-vehicle network 126.

In accordance with an embodiment, the device 102 may be configured to determine an operating mode of the device 102, based on the received first set of input values and the second set of input values. The device 102 may be configured to utilize current location information of the vehicle 106 and a motion status of the vehicle 106 to determine the operating mode. The operating mode may be one of the various operating modes described in detail in FIG. 2A.

In accordance with an embodiment, the device 102 may be configured to control one or more functions of the vehicle 106, based on the determined operating mode of the device 102. In accordance with different embodiments, the device 102 may perform different functions in different operating modes, based on the first set of input values (such as vital health data of the first user 128) received from the one or more wearable devices 104. For example, vital health data of the first user 128 may be used to perform authentication of the first user 128, when the one or more wearable devices 104 associated with the first user 128 are detected within a first proximity range from the device 102. The determined mode in this case may be an about-to-drive mode. However, the same vital health data of the first user 128 may be used to monitor the heath of the first user 128 in other determined modes, such as in a home mode or an outside driving mode.

In an instance, based on the determined operating mode, such as such as an about-to drive mode, the device 102 may be configured to control one or more functions, such as a dynamic configuration of pre-defined personalization settings associated with the first user 128, at the vehicle 106. Such dynamic configuration may occur based on an authentication of the first user 128 by the device 102. The one or more functions may further include adjustment of vehicle internal ambience, adjustment of a vehicle seat, and/or adjustment of a position of a vehicle mirror of the vehicle 106. The one or more functions may correspond to open or close a vehicle door, control vehicle ignition, and/or control the speed of the vehicle 106. The one or more functions may further include synchronization of personal data collected from the one or more wearable devices 104 or a portable device, such as a smartphone of the first user 128, with the device 102.

In another instance, based on the determined operating mode, such as a user-critical health mode, the device 102 may be configured to communicate with the one or more external devices, such as the mobile device 108, associated with the caregiver 132. The device 102 may be configured to further communicate with the medical care center 116 and/or the ambulance service provider 118. In another instance, based on the determined operating mode, such as in an outside driving mode, device 102 may be configured to communicate with the communication device 110, which may be situated in the police control room 112. In another instance, based on the determined operating mode, such as in a vehicle-breakdown mode, the device 102 may be configured to communicate with the vehicle breakdown service provider 120.

Figure 2A:
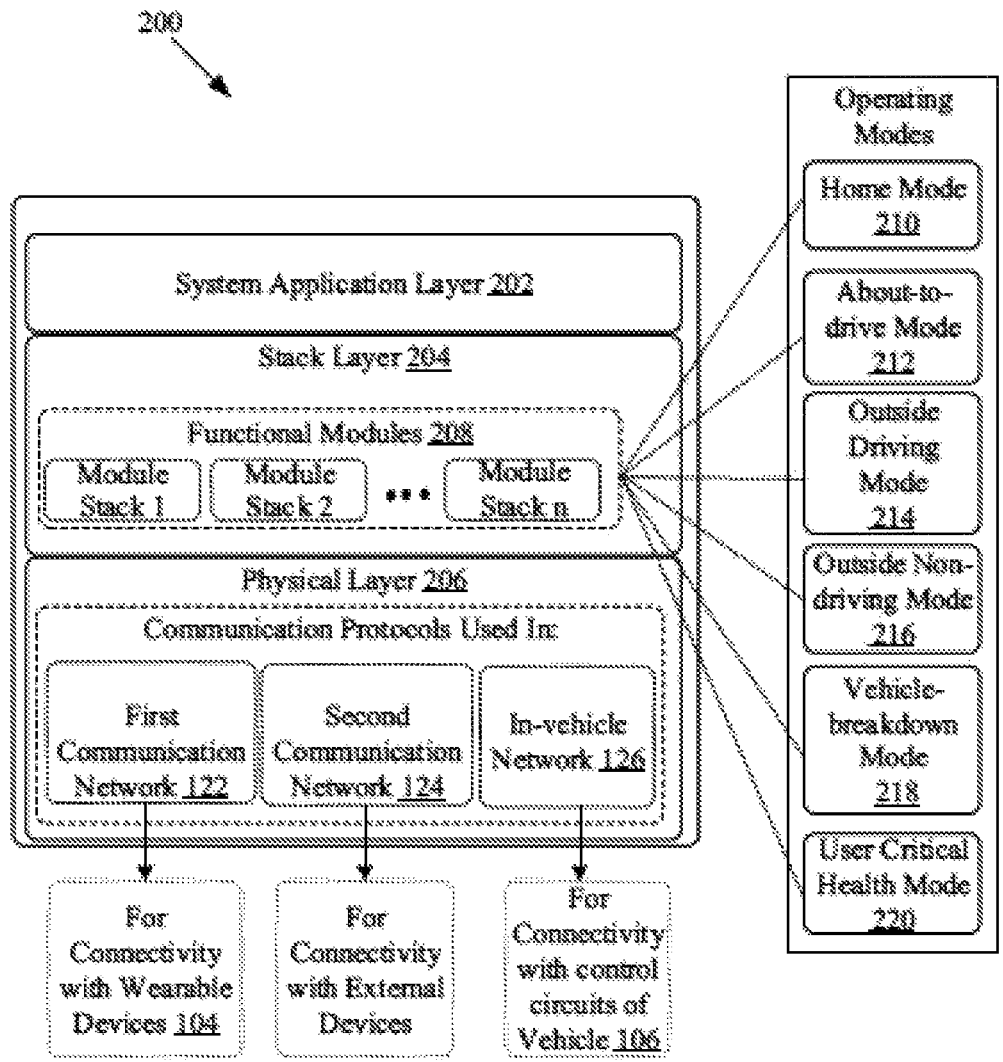
FIG. 2A is a block diagram that illustrates an exemplary high-level architecture of a device that manages interaction with one or more control circuits in a vehicle and one or more wearable devices, in accordance with an embodiment of the disclosure.

FIG. 2A is a block diagram that illustrates an exemplary high-level architecture 200 of the device 102 that may manage interaction with one or more control circuits in a vehicle (such as the vehicle 106) and the one or more wearable devices 104, in accordance with an embodiment of the disclosure. FIG. 2A is explained in conjunction with elements from FIG. 1. With reference to FIG. 2A, there is shown the high-level architecture 200 of the device 102. The high-level architecture 200 may comprise a system application layer 202, a stack layer 204, and a physical layer 206. The stack layer 204 may include functional modules 208. The functional modules 208 may be associated with various operating modes, such as a home mode 210, an about-to-drive mode 212, an outside driving mode 214, an outside non-driving mode 216, a vehicle-breakdown mode 218, and/or a user-critical health mode 220.

The system application layer 202 may refer to a topmost layer that may be used for the system initialization, such as initialization of the device 102. The system application layer 202 may support end-user processes. The system application layer 202 may provide options and/or an interface for configuration changes related to the functional modules 208 of the stack layer 204.

The stack layer 204 may comprise one or more module stacks, such as the functional modules 208. The stack layer 204 may perform various functions or control various functions of the vehicle 106, in accordance with an operating mode of the device 102. The functionalities of the device 102 may be performed by use of the functional modules 208. In accordance with an embodiment, the functional modules 208 may be implemented as one or more module stacks, such as a health module stack, an authentication module stack, a fit-to-drive module stack, a personalization module stack, and/or a vehicle infrastructure module stack. The health module stack may be used by the device 102 to receive and process vital heath data from the one or more wearable devices 104. The authentication module stack may be used by the device 102, to receive and process the first set of input values for user authentication. The fit-to-drive module stack may be used by the device 102 to receive and process both the first set of input values (such as blood alcohol level data), and the second set of input values (such as vehicle health diagnostics data). The device 102 may determine a fit-to-drive condition of both the vehicle user, such as the first user 128, and the vehicle 106, before start of each drive for the vehicle 106, by use of the fit-to-drive module stack. The personalization module stack may be used by the device 102 to process pre-stored personalization settings associated with different pre-registered vehicle users at the device 102. The vehicle infrastructure module stack may be used by the device 102 to send one or more control commands to the one or more control units of the vehicle 106, based on the processing of the first set of input values and the second set of input values by the other module stacks.

The physical layer 206 refers to a bottom layer that supports an electrical or mechanical interface to a physical medium. The physical layer 206 supports various communication protocols for use in the first communication network 122, the second communication network 124, and the in-vehicle network 126. For example, the physical layer 206 supports the communication protocols, such as Bluetooth, NFC, Wi-Fi, ZigBee, and/or USB in the first communication network 122, for connectivity of the device 102 with the one or more wearable devices 104. The physical layer 206 also supports the communication protocols, such as 3G, 4G, and/or LTE in the second communication network 124, for connectivity of the device 102 with the one or more external devices described previously in FIG. 1. In accordance with an embodiment, the 3G, 4G, and/or LTE protocols may be used by the device 102 when a wireless communication system of the vehicle 106, such as a telematics unit, fails to send data to the outside of the vehicle 106. The physical layer 206 also supports the communication protocols, such as the CAN, the LIN, and the Ethernet in the in-vehicle network 126, for connectivity of the device 102 with the one or more control circuits of the vehicle 106.

The home mode 210 may correspond to a condition or a situation when a vehicle, such as the vehicle 106, associated with the device 102, is in a standstill situation parked at a pre-configured location, such as a residence location (a home parking lot), of the first user 128. Further, the home mode 210 refers to a condition or a situation when the health of the vehicle 106 is normal, and no fault or breakdown is detected at the vehicle 106. In the home mode, the device 102 may receive vital health data from the one or more wearable devices 104. The home mode 210 may further refer to a situation when the received vital health data of the first user 128 indicates that a medical condition of the first user 128 is within normal limits.

The about-to-drive mode 212 may correspond to a condition or a situation when a vehicle user, such as the first user 128, is in a vicinity (such as a first proximity range), of the vehicle 106. The about-to-drive mode 212 may be activated just before the start of drive when the vehicle user wants to drive the vehicle 106. In the about-to-drive mode 212, the device 102 may receive vital health data from the one or more wearable devices 104, and use the received vital health data for user authentication purposes.

The outside driving mode 214 may correspond to a condition or a situation when a vehicle, such as the vehicle 106 associated with the device 102, is in motion and not parked at the pre-configured location (such as the home parking location), of the first user 128. Further, the outside driving mode 214 refers to a condition or a situation when the health of the vehicle 106 is normal and no fault or breakdown is detected at the vehicle 106. In the outside driving mode, the device 102 may receive vital health data from the one or more wearable devices 104.

The outside non-driving mode 216 may correspond to a condition or a situation when a vehicle, such as the vehicle 106, associated with the device 102, is not in motion and not parked at the pre-configured location (such as the home parking location), of the first user 128. The outside non-driving mode 216 may correspond to another condition or another situation when the health of the vehicle 106 is normal and no fault or breakdown is detected at the vehicle 106. The outside non-driving mode 216 may further may correspond to yet another condition or another situation when the vehicle 106 is stuck up in a traffic signal, a traffic jam, or parked at other location different from the pre-configured location (such as the home parking location). In the outside non-driving mode 216, the device 102 may receive vital health data from the one or more wearable devices 104.

The vehicle-breakdown mode 218 may correspond to a condition or a situation when the health of the vehicle 106 is not normal, and a breakdown is detected at the vehicle 106. The breakdown may be due to one or more of a faulty sensor, a mechanical fault, an electrical fault, and/or a weather condition. In the vehicle-breakdown mode 218, the vehicle 106 may be in a standstill situation, in motion, parked at the pre-configured location (such as the home parking location), a service center, or other such location.

In the user-critical health mode 220, the device 102 may receive vital health data from the one or more wearable devices 104, worn by the first user 128. In such a case, the first user 128 may be a patient with medical implants. The first user 128 may be suffering from critical diseases or physiological problems (such as heart diseases or urologic problems), and may need continuous post-operative monitoring. The user-critical health mode 220 may correspond to a condition or a situation when the received vital health data of the first user 128 indicates a critical medical condition of the first user 128. The received vital health data may comprise a set of medical values (sensor readings) that may be compared with health thresholds or one or more safety limits preset by a healthcare professional, such as a doctor, a paramedic, and/or the caregiver 132.

Figure 2B:
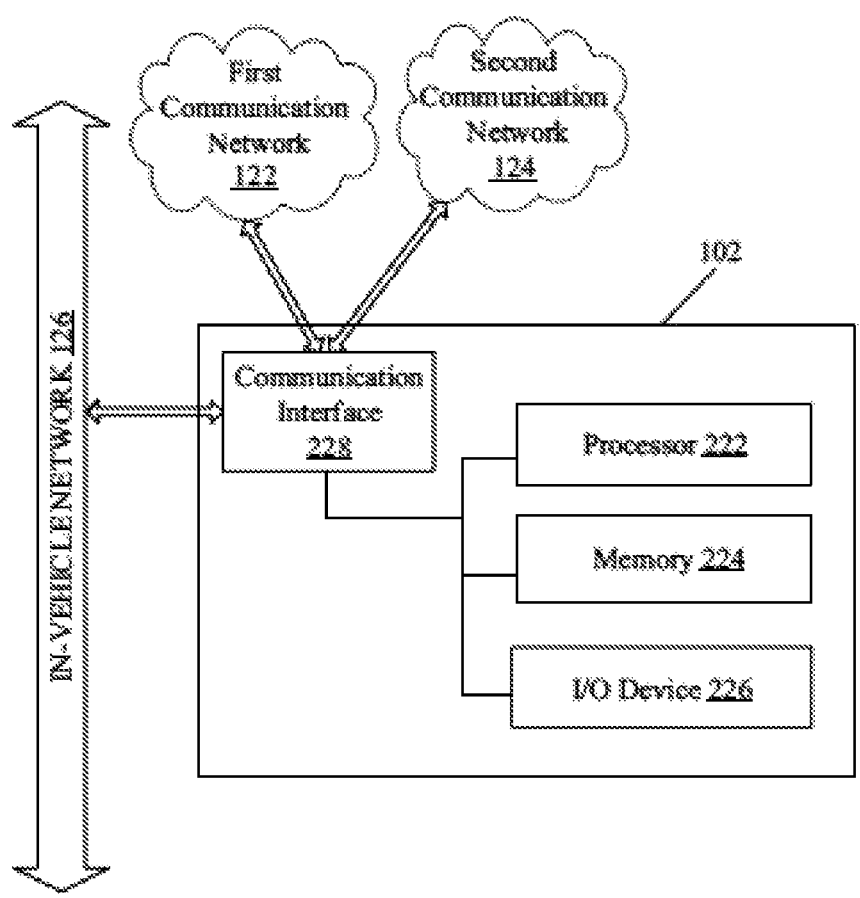
FIG. 2B is a block diagram that illustrates an exemplary device, in accordance with an embodiment of the disclosure.

FIG. 2B is a block diagram that illustrates an exemplary device, in accordance with an embodiment of the disclosure. FIG. 2B is explained in conjunction with elements from FIG. 1 and FIG. 2A. With reference to FIG. 2B, there is shown the device 102. The device 102 may comprise one or more processors, such as a processor 222, a memory 224, one or more input/output (I/O) devices, such as I/O device 226, and a communication interface 228. The processor 222 may be communicatively coupled to the memory 224, the I/O device 226, and the communication interface 228.

The processor 222 may comprise suitable logic, circuitry, interfaces, and/or code that may be configured to execute a set of instructions stored in the memory 224. The processor 222 may be implemented based on a number of processor technologies known in the art. Examples of the processor 222 may be an X86-based processor, X86-64-based processor, a Reduced Instruction Set Computing (RISC) processor, an Application-Specific Integrated Circuit (ASIC) processor, a Complex Instruction Set Computing (CISC) processor, a central processing unit (CPU), an Explicitly Parallel Instruction Computing (EPIC) processor, a Very Long Instruction Word (VLIW) processor, and/or other processors or circuits.

The memory 224 may comprise suitable logic, circuitry, and/or interfaces that may be configured to store a machine code and/or a set of instructions executable by the processor 222. The memory 224 may be configured to store the one or more module stacks, such as the functional modules 208. The memory 224 may be further configured to store one or more pre-configured user-settings associated with the first user 128. The memory 224 may be further configured to store operating systems and associated applications. Examples of implementation of the memory 224 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 226 may comprise suitable logic, circuitry, interfaces, and/or code that may be configured to receive an input from and provide an output to a user, such as the first user 128. Examples of the input devices may include, but are not limited to, a hardware button on the device 102, a software button on an interface of the device 102, a touch screen, a microphone, a motion sensor, and/or a light sensor. Examples of the output devices may include, but are not limited to, a display and/or a speaker.

The communication interface 228 may comprise suitable logic, circuitry, interfaces, and/or code that may be configured to communicate with the one or more wearable devices 104, via the first communication network 122. The communication interface 228 may be further configured to communicate with the one or more external devices, such as the mobile device 108, the communication device 110, the cloud server 114, the medical care center 116, the ambulance service provider 118, and the vehicle breakdown service provider 120, via the second communication network 124. The communication interface 228 may be further configured to communicate with one or more control circuits, such as the internal ECUs, in the vehicle 106, via the in-vehicle network 126. The communication interface 228 may implement known technologies to support wired or wireless communication of the device 102 with first communication network 122, the second communication network 124, and the in-vehicle network 126. The communication interface 228 may include various components, not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer. The communication interface 228 may communicate via wired or wireless communication by use of the various communication protocols, as described previously in FIG. 1, with regard to the first communication network 122, the second communication network 124, and the in-vehicle network 126. The various communication protocols used for the wired or wireless communication may be supported by the physical layer 206, as described in FIG. 2A.

In operation, the processor 222 may be configured to receive a first set of input values from the one or more wearable devices 104. The one or more wearable devices 104 may be worn by the first user 128, such as an owner of the vehicle 106. The one or more wearable devices 104 may be communicatively coupled to the device 102 used in the vehicle 106, via the first communication network 122. The communicative coupling may occur by use of various communication protocols, such as the Bluetooth protocol, supported by the physical layer 206.

In accordance with an embodiment, the first set of input values may comprise vital health data of the first user 128. Examples of the vital health data may include, but are not limited to, electrocardiogram (ECG), heart rate, respiratory rate, blood oxygen level (such as peripheral capillary oxygen saturation (SPO2)), blood pressure, and/or body temperature of the first user 128. The first set of input values may further comprise blood alcohol content (BAC) information of the first user 128 that may be sensed by the blood alcohol sensor of the one or more wearable devices 104. In accordance with an embodiment, the first set of input values may further include vital health data of the first user 128, received from the electronic implants of the first user 128. In an instance, the first user 128 may have pacemakers implanted to sense cardiac intrinsic electrical activity and to pace the cardiac chambers of the heart. In an instance, the first user 128 may have an implantable cardioverter-defibrillator (ICD) for cardiac resynchronization therapy. Such implants may provide vital health data, such as ventricular heart rate.

In accordance with an embodiment, the processor 222 may be configured to receive a second set of input values from the one or more vehicle sensors embedded in the vehicle 106. The second set of input values may comprise vehicle data of the vehicle 106. The vehicle data may comprise a motion status, a geospatial position, a yaw rate, a speed, a direction of travel, a steering angle, and/or a rate-of-change of speed of the vehicle 106. The vehicle data may further include a vehicle positional accuracy data, a brake system status, a status of a vehicle stability system, and/or other vehicle parameters of the vehicle 106.

In accordance with an embodiment, the processor 222 may be configured to determine a data type of the received first set of input values and the second set of input values. The data type of the first set of input values may correspond to heath data of the first user 128. The data type of the second set of input values may correspond to heath data of the vehicle 106.

In accordance with an embodiment, the processor 222 may be configured to determine an operating mode, based on the received first set of input values and the second set of input values. The processor 222 may be configured to utilize at least a current location information of the vehicle 106, a motion status of the vehicle 106, the determined data type, and/or a distance of the one or more wearable devices 104 from the device 102, for the determination of the various operating modes. The operating modes have been described in detail in FIG. 2A.

In accordance with an embodiment, the processor 222 may be configured to control one or more functions of the vehicle 106 based on the determined operating mode of the device 102. In accordance with an embodiment, the processor 222 may be configured to control one or more functions of the vehicle 106, based on the determined data type and one or more pre-configured user-settings associated with the first user 128.

In accordance with an embodiment, when the determined operating mode is the home mode 210, the processor 222 may be configured to monitor vital health data received from the one or more wearable devices 104. The processor 222 may be configured to detect whether the received vital health data is in accordance with preset health thresholds, as per the user (such as the first user 128), or within one or more preset medical safety limits. In instances when the received vital health data is not in accordance with the preset health thresholds and/or not within the one or more preset medical safety limits, the processor 222 may be configured to switch the operating mode of the device 102 from the home mode 210 to the user-critical health mode 220.

In accordance with an embodiment, when the received vital health data is in accordance the preset health thresholds, and/or within the one or more preset medical safety limits, the processor 222 may be configured to detect whether the one or more wearable devices 104 are within a preset first proximity range, such as within a range of "1 meter", from the device 102. In instances when the one or more wearable devices 104 are detected within the preset first proximity range from the device 102, it may be an indication that the first user 128 wants to drive the vehicle 106. The processor 222 may then switch the operating mode at the device 102 from the home mode 210 to the about-to-drive mode 212. Further, in instances when the one or more wearable devices 104 are not detected within the preset first proximity range from the device 102, it may be an indication that the first user 128 may not want to drive the vehicle 106. In such instances, the processor 222 may periodically monitor the vital heath data received from the one or more wearable devices 104, which may be communicatively coupled to the device 102, via the first communication network 122.

In accordance with an embodiment, when the determined operating mode is the about-to-drive mode 212, the processor 222 may be configured to authenticate a user, such as the first user 128, based on the first set of input values, such as the ECG data of the first user 128. The authentication may be useful to validate the first user 128 to drive the vehicle 106. For example, based on the authentication, the processor 222 may be configured to send a command to a body control module of the vehicle 106 to open or close the door of the vehicle 106.

In accordance with an embodiment, the processor 222 may be configured to perform multiple-user authentication. For example, the vehicle 106 may be a rental car that has multiple drivers. The processor 222 may be configured to validate each driver based on a comparison of received vital heath data of each of the drivers with corresponding profile pre-stored at the memory 224 or at the cloud server 114.

In accordance with an embodiment, the processor 222 may be configured to detect the alcohol level associated with the first user 128 with respect to a preset safety limit. Such determination is used by the processor 222, to decide whether a user, such as the first user 128, is fit or unfit to drive the vehicle 106. When the determined alcohol level is greater than the preset safety limit (such as an intoxication level), and when the determined operating mode is the about-to-drive mode 212, the processor 222 may send a control command to the body control module of the vehicle 106 to prohibit the door of the vehicle 106 to be opened. The command may be sent by the device 102 to restrict entry of the first user 128 into the vehicle 106.

In accordance with an embodiment, the processor 222 may send one or more commands to multiple ECUs, such as the body control module and the engine control unit, of the vehicle 106 to open the door of the vehicle 106. In such a case, the door of the vehicle 106 may be opened, however the ignition key or button may be disabled so that first user 128 is unable to start the vehicle 106. Such one or more commands may restrict the ability of the vehicle 106 to be driven by the first user 128 to ensure the safety of the first user 128 when the determined alcohol level is greater than the preset safety limit. Thus, the ability to drive may be restricted even when the first user 128 is authenticated, as described previously.

In accordance with an embodiment, when the determined alcohol level is lower than the preset safety limit, the processor 222 may send one or more control commands to one or more ECUs, such as the body control module and/or a powertrain control system, of the vehicle 106. The one or more control commands may be sent to open the door of the vehicle 106 and/or to ignite of an engine of the vehicle 106, to start the vehicle 106 in the about-to-drive mode 212. Alternatively, the ignition key or button may be enabled so that first user 128 can start the vehicle 106.

In accordance with an embodiment, the processor 222 may be configured to dynamically configure pre-defined personalization settings associated with the first user 128, based on the authentication of the first user 128 in the about-to-drive mode 212. The dynamic configuration may correspond to a mechanical or a non-mechanical configuration at the vehicle 106. Examples of mechanical configuration may include, but are not limited to, adjustment of one or more vehicle seats of the vehicle 106, adjustment of a position of various vehicle mirrors (such as an electric-operated outside rear view mirror (ORVM) of the vehicle 106), and/or other mechanical movements at the vehicle 106. Examples of the non-mechanical configurations or changes may include, but are not limited to, auto-adjustment of one or more control systems of the vehicle 106, such as temperature or humidity control inside the vehicle 106, auto-loading of songs preferences of a vehicle user, such as the first user 128, at an infotainment unit of the vehicle 106, and/or synchronization of personal data collected from a portable device (such as a smartphone) associated with the first user 128.

In accordance with an embodiment, the processor 222 may be configured to determine vehicle health of the vehicle 106 by use of an on-board diagnostics (OBD) interface before start of a drive in the about-to-drive mode 212. The processor 222 may be configured to indicate whether the vehicle 106 is fit or unfit to drive, based on the output received form the OBD interface. The output may be a visual, haptic, or audio output at the vehicle 106. In instances when a fault is detected at the vehicle 106, the processor 222 may be configured to switch the about-to-drive mode 212 to the vehicle-breakdown mode 218 at the device 102. Further, in instances when no fault is detected at the vehicle 106 based on the determined vehicle health, the processor 222 may be configured to switch the operating mode of the device 102 from the about-to-drive mode 212 to the outside driving mode 214.

In accordance with an embodiment, when the determined operating mode is the outside driving mode 214, the processor 222 may be configured to communicate with the one or more wearable devices 104 periodically, such as "every 30 seconds". The periodic communication with the one or more wearable devices 104 may occur when the vehicle 106 is in motion. Based on the periodic communication, the processor 222 may confirm the presence of an authenticated user, such as first user 128, in the vehicle 106. In instances when the authenticated first user 128 is not detected in the vehicle 106 when the operating mode is the outside driving mode 214, the processor 222 may be configured to communicate a theft alert to the communication device 110, situated at the police control room 112. The processor 222 may be configured to locate the police control room 112, within a vicinity of the vehicle 106 when the authenticated first user 128 is not detected in the vehicle 106 when the operating mode is the outside driving mode 214.

In accordance with an embodiment, when an authenticated user is detected inside the vehicle 106 when the operating mode is the outside driving mode 214, the processor 222 may be configured to send a temperature change signal to an ECU of the vehicle 106, at pre-defined time intervals. The temperature change signal may be sent to adjust the temperature inside the vehicle 106, as per user preferences of the authenticated user, such as the first user 128. The adjustment of temperature may occur based on the received body temperature values from a temperature sensor of the one or wearable devices 104 of the first user 128.

In accordance with an embodiment, the monitoring of the health of the first user 128 may also performed in the outside driving mode 214, based on the vital health data received from the one or more wearable devices 104. The processor 222 may be configured to detect an abnormal medical condition of the first user 128, based on vital health data received from the one or more wearable devices 104 or a portable electronic device associated with the first user 128. The processor 222 may be configured to determine a severity level of the detected abnormal medical condition based a predetermined health threshold associated with first user 128. The severity level of the detected abnormal medical condition may also be determined and validated by use of the preset medical safety limits at the device 102.

In accordance with an embodiment, when the determined severity level indicates a critical health condition, the processor 222 may be configured to switch the operating mode of the device 102 from the outside driving mode 214 to the user-critical health mode 220. In instances when the determined severity level does not indicate a critical health condition, the processor 222 may be configured to communicate a health alert notification to an electronic device, such as the mobile device 108, associated with the caregiver 132. The health alert notification may be sent together with the current location information of the first user 128 when the operating mode of the device 102 is the outside driving mode 214.

In accordance with an embodiment, the processor 222 may be configured to receive instructions from the caregiver 132, via the second communication network 124. The instructions from the caregiver 132 may be received at the device 102, by use of the communication interface 228. The instructions may be received to control one or more functions, such as temperature and humidity adjustment, of the vehicle 106. The instructions may be further utilized to remotely handle the detected abnormal medical condition of the first user 128 when the operating mode of the device 102 is the outside driving mode 214.

In accordance with an embodiment, based on the determined severity level, the processor 222 may be configured to control vehicle speed when the determined operating mode of the device 102 is the outside driving mode 214 and/or the user-critical health mode 220. In accordance with an embodiment, based on the determined severity level, the processor 222 may be configured to send a health alert notification with current location information of the first user 128 to the medical care center 116 (such as a hospital), and/or the ambulance service provider 118 when the determined operating mode of the device 102 is the user-critical health mode 220. In accordance with an embodiment, based on the determined severity level, the processor 222 may be configured to generate a guidance for the first user 128, when the determined operating mode of the device 102 is the user-critical health mode 220. In such a case, the guidance is generated to enable the first user 128 to reach a hospital nearest the vehicle 106.

In accordance with an embodiment, the processor 222 may be configured to automatically control steering of the vehicle 106, to drive the vehicle 106 (in an autonomous driving mode) to the medical care center 116 in a vicinity of the vehicle 106. The automatic control of the steering of the vehicle 106 may occur when the first user 128 is detected to be in a critical health condition which prohibits the first user 128 to drive the vehicle 106.

In accordance with an embodiment, when the determined operating mode of the device 102 is the outside non-driving mode 216, the processor 222 may be configured to transfer the authentication to another device associated with a second user, such as the second user 130, for a pre-defined time interval. The transfer of authentication may enable the second user 130, such as a valet, to gain entry into the vehicle 106 and move the vehicle 106 up to a pre-defined distance. In accordance with an embodiment, the authentication may be wirelessly transmitted from one of the one or more wearable devices 104, such as a smart watch, by the first user 128 to the other device (such as a smartphone) associated with the second user 130, via an authentication transfer feature.

In accordance with an embodiment, the first user 128 may provide an input at a wearable device of the one or more wearable devices 104 to enable the authentication transfer feature. The first user 128 may give the wearable device to the second user 130. The processor 222 may recognize that the authentication transfer feature is enabled on the wearable device. The processor 222 may be configured to control opening of a door of the vehicle 106. The processor 222 may be further configured to control vehicle ignition to start the vehicle 106 to allow the second user 130 to drive the vehicle 106. The processor 222 may be configured to determine the enabled authentication transfer feature and the control of the opening of the door and vehicle ignition of the vehicle 106 when the determined operating mode is the outside non-driving mode 216, and when the wearable device is detected in the vicinity of the device 102. For example, the first user 128 may ask the second user 130 (such as the valet), to park the vehicle 106. During valet parking, the first user 128 may set a time and radius limit. Consequently, the vehicle 106 may be moved by the second user 130 to a certain distance and for a certain duration in accordance with the radius limit and the time set by the first user 128.

In accordance with an embodiment, the processor 222 may be configured to control temperature inside the vehicle 106, when the determined operating mode of the device 102 is the outside non-driving mode 216. The temperature inside the vehicle 106 may be controlled based on the current body temperature of the first user 128, received from the one or more wearable devices 104 when the first user 128 is outside the vehicle 106. The device 102 may then send one or more commands to a suitable ECU of the vehicle 106. Accordingly, based on the commands, the temperature of the vehicle 106 may be adjusted, as per the current body temperature of first user 128. Hence, the first user 128 may not experience a thermal shock when the first user 128 enters the vehicle 106.

In accordance with an embodiment, when the determined operating mode is the vehicle-breakdown mode 218, the processor 222 may be configured to communicate vehicle breakdown information to the vehicle breakdown service provider 120. The contact details of the vehicle breakdown service provider 120 may be pre-configured at the device 102, and pre-stored at the memory 224. The vehicle breakdown information may include a cause of the vehicle-breakdown, a customized message provided by the first user 128, location information of the vehicle 106, and/or date and time of vehicle-breakdown of the vehicle 106. The processor 222 may be configured to receive a confirmation response at the device 102 from the vehicle breakdown service provider 120 in the vehicle-breakdown mode 218. The confirmation response may be an acknowledgment message for the receipt of the vehicle breakdown information.

Figure 3:
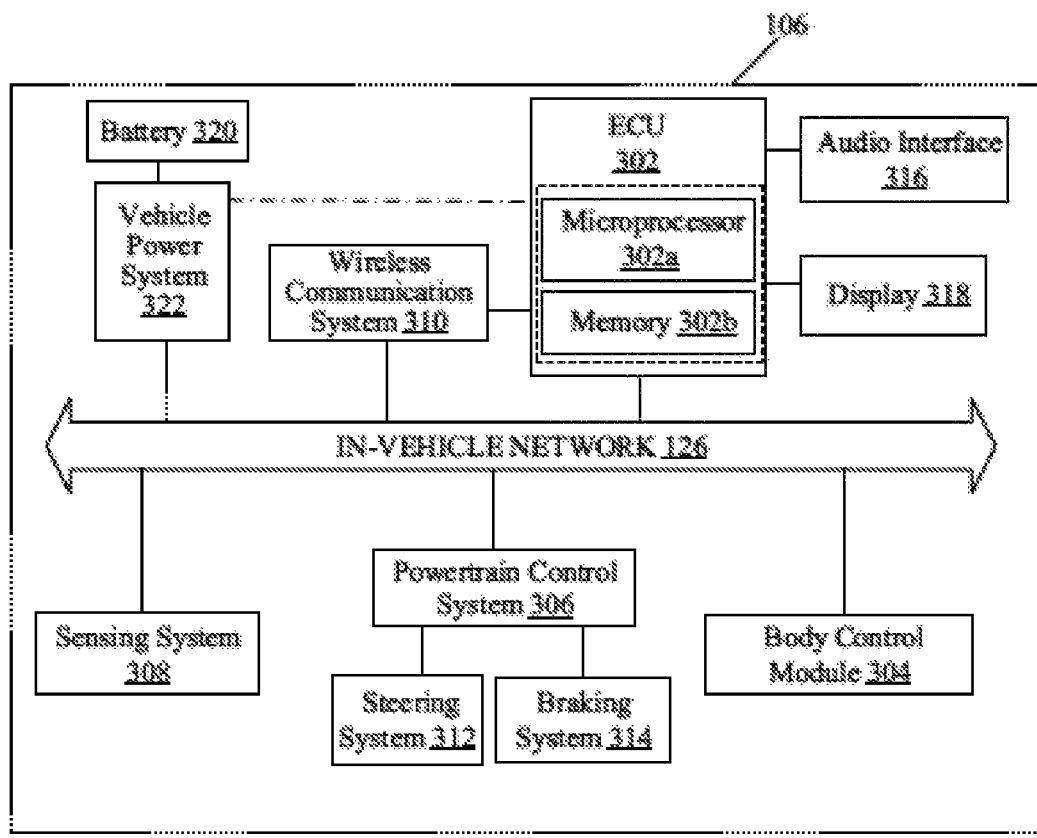
FIG. 3 is a block diagram that illustrates various exemplary components or systems of a vehicle, in accordance with an embodiment of the disclosure.

FIG. 3 is a block diagram that illustrates various exemplary components or systems of a vehicle, in accordance with an embodiment of the disclosure. FIG. 3 is explained in conjunction with elements from FIGS. 1, 2A, and 2B. With reference to FIG. 3, there is shown various control units, systems or components of the vehicle 106. The vehicle 106 may comprise an electronic control unit (ECU) 302, a body control module 304, a powertrain control system 306, a sensing system 308, and a wireless communication system 310. The ECU 302 may include a microprocessor 302a and a memory 302b. The vehicle 106 may further comprise a steering system 312 and a braking system 314, associated with the powertrain control system 306. The vehicle 106 may also comprise an audio interface 316, a display 318, and the wireless communication system 310, associated with the ECU 302. There is further shown a battery 320 associated with a vehicle power system 322.

The various control units, components, and/or systems of the vehicle 106 may be communicatively coupled with each other, via the in-vehicle network 126, such as a vehicle area network (VAN), and/or an in-vehicle data bus. The microprocessor 302a may be communicatively coupled to the memory 302b, the wireless communication system 310, the audio interface 316, the display 318, and the sensing system 308, via the in-vehicle network 126. In accordance with an embodiment, the microprocessor 302a may be operatively connected to the body control module 304 and the powertrain control system 306. A person with ordinary skill in the art will understand that the vehicle 106 may also include other suitable components or systems, but for brevity, those components, or systems, which are used to describe and explain the function and operation of the present disclosure, are illustrated herein.

The ECU 302 may include suitable logic, circuitry, interfaces, and/or code that may be configured to be communicatively coupled to other ECUs of the vehicle 106. The ECU 302 may be configured to receive one or more control commands from the communication interface 228 (FIG. 2B) of the device 102, via the in-vehicle network 126. The ECU 302 may be configured to further communicate the received one or more control commands to other ECUs, components, or systems of the vehicle 106. The ECU 302 may comprise the microprocessor 302a and the memory 302b.

The microprocessor 302a may comprise suitable logic, circuitry, interfaces, and/or code that may be configured to execute a set of instructions stored in the memory 302b. Examples of the microprocessor 302a may be an X86-based processor, a Reduced Instruction Set Computing (RISC) processor, an Application-Specific Integrated Circuit (ASIC) processor, a Complex Instruction Set Computing (CISC) processor, an Explicitly Parallel Instruction Computing (EPIC) processor, a Very Long Instruction Word (VLIW) processor, a microcontroller, a central processing unit (CPU), a graphics processing unit (GPU), a state machine, and/or other processors or circuits.

The memory 302b may comprise suitable logic, circuitry, and/or interfaces that may be configured to store a machine code and/or a set of instructions with at least one code section executable by the microprocessor 302a. The memory 302b may be further operable to store the functional modules 208 that may include the one or more module stacks (FIG. 2A). Examples of implementation of the memory 302b may include, but are not limited to, Electrically Erasable Programmable Read-Only Memory (EEPROM), Random Access Memory (RAM), Read Only Memory (ROM), Hard Disk Drive (HDD), Flash memory, a Secure Digital (SD) card, Solid-State Drive (SSD), and/or CPU cache memory.

The body control module 304 may refer to another electronic control unit that comprises suitable logic, circuitry, interfaces, and/or code that may be configured to control a central door locking system of the vehicle 106. The body control module 304 may be configured to receive a command from the device 102 or the ECU 302. Subsequently, the body control module 304 may relay the command to other suitable vehicle systems or components, such as the central door locking system, for access control of the vehicle 106.

The powertrain control system 306 may refer to an onboard computer of the vehicle 106 that controls operations of an engine and a transmission system (when provided) of the vehicle 106. The powertrain control system 306 may control ignition system, fuel injection, emission systems, and/or operations of the transmission system (when provided) and the braking system 314.

The sensing system 308 may comprise one or more vehicle sensors provided in the vehicle 106. The sensing system 308 may be operatively connected to the ECU 302 or the device 102, via the in-vehicle network 126, to provide input signals to the processor 222. One or more network interfaces, such as a CAN interface, may be provided in the sensing system 308, to connect to the in-vehicle network 126. Examples of the one or more vehicle sensors of the sensing system 308 may include, but are not limited to, a radio detection and ranging (RADAR) device, a light detection and ranging (LIDAR) device, an image sensor, a vehicle speed sensor, an odometric sensor, a yaw rate sensor, a speedometer, a global positioning system (GPS), a steering angle detection sensor, a vehicle travel direction detection sensor, a magnometer, a touch sensor, and/or an infrared sensor. The one or more vehicle sensors of the sensing system 308 may be configured to detect a motion status, a direction of travel, location information, a steering angle, a yaw rate, a speed, and/or a rate-of-change of speed of the vehicle 106.

The wireless communication system 310 may comprise suitable logic, circuitry, interfaces, and/or code that may be configured to communicate with the one or more external devices, such as the mobile device 108, the communication device 110, the cloud server 114, the medical care center 116, the ambulance service provider 118, and/or the vehicle breakdown service provider 120, under the control of the processor 222. Such communication with the one or more external devices may occur by use of the second communication network 124. The wireless communication system 310 may include various components that may include, but are not limited to, an antenna, a telematics unit, a radio frequency (RF) transceiver, one or more amplifiers, one or more oscillators, a digital signal processor, a near field communication (NFC) circuitry, a coder-decoder (CODEC) chipset, and/or a subscriber identity module (SIM) card. The wireless communication system 310 may communicate with networks, such as the second communication network 124 under the control of the processor 222, via communication protocols, as described previously in the second communication network 124 (FIG. 1).

The steering system 312 may be associated with the powertrain control system 306. The steering system 312 may include a steering wheel and/or an electric motor (provided for a power-assisted steering) that may be used by a vehicle user, such as the first user 128, to control movement of the vehicle 106. In accordance with an embodiment, the movement or steering of the vehicle 106 may be automatically controlled when the vehicle 106 is in autonomous mode. Examples of the steering system 312 may include, but are not limited to, an autonomous steering control, a power-assisted steering system, a vacuum/hydraulic-based steering system, an electro-hydraulic power-assisted system (EH-PAS), or a "steer-by-wire" system, known in the art.

The braking system 314 may be used to stop or slow down the vehicle 106 by application of frictional forces. The braking system 314 may be configured to receive a command from the powertrain control system 306, under the control of the microprocessor 302a, when the vehicle 106 is in an autonomous mode or a semi-autonomous mode.

The audio interface 316 may be connected to a speaker, a chime, a buzzer, or other such device that may be operable to generate a sound. The audio interface 316 may also be connected to a microphone or other such device to receive a voice input from an occupant of the vehicle 106, such as the first user 128.

The display 318 may refer to a touch screen that may receive an input from the first user 128 and to display various types of information to occupants of the vehicle 106. The audio interface 316 may be a part of an infotainment unit or a head unit of the vehicle 106. In accordance with an embodiment, in-vehicle communication of audio/video data for multimedia components may occur by use of Media Oriented Systems Transport (MOST) multimedia network protocol of the in-vehicle network 126. Examples of the display 318 may include, but are not limited to, a display of the head unit, a heads-up display (HUD), a head-up display with an augmented reality system (AR-HUD), a driver information console (DIC), a projection-based display, a see-through display, a smart-glass display, and/or an electrochromic display. The vehicle 106 may include other input/output (I/O) devices that may be configured to communicate with the microprocessor 302a and/or the processor 222.

The in-vehicle network 126 may include a medium through which the various components or systems of the vehicle 106, such as the ECU 302, the body control module 304, the powertrain control system 306, the sensing system 308, and/or the wireless communication system 310, may communicate with each other. The in-vehicle network 126 may facilitate access control and/or communication between the ECU 302, other internal ECUs of the vehicle 106, and the device 102. One or more communication interfaces, such as the CAN interface, a Local Interconnect Network (LIN) interface, a Media Oriented Systems Transport (MOST) interface, may be used by the various components or systems of the vehicle 106 to connect to the in-vehicle network 126. In accordance with an embodiment, in-vehicle communication of audio/video data for multimedia components may occur by use of Media Oriented Systems Transport (MOST) multimedia network protocol of the in-vehicle network 126. The MOST based network may be a separate network from the controller area network (CAN). The MOST based network may use a plastic optical fiber (POF). In accordance with an embodiment, the MOST based network, the CAN, and other in-vehicle networks may co-exist in the vehicle 106. In accordance with an embodiment, the processor 222 may be configured to receive the second set of input values directly from the in-vehicle network 126. Alternatively, the processor 222 may be configured to receive the second set of input values, which correspond to the vehicle data, from the ECU 302. Other aspects or details of the in-vehicle network 126 has been described previously in FIG. 1.

The battery 320 may be source of electric power for one or more electric circuits or loads (not shown). For example, the loads may include, but are not limited to various lights, such as headlights and interior cabin lights, electrically powered adjustable components, such as vehicle seats, mirrors, windows or the like, and/or other in-vehicle infotainment system, such as radio, speakers, electronic navigation system, electrically controlled, powered and/or assisted steering, such as the steering system 312. The battery 320 may be a rechargeable battery. The battery 320 may be a source of electrical power to the ECU 302 (shown by dashed lines), the one or more sensors of the sensing system 308, and/or one or more hardware units, such as the display 318, of the in-vehicle infotainment system. The battery 320 may be a source of electrical power to start an engine of the vehicle 106 by selectively providing electric power to an ignition system (not shown) of the vehicle 106.

The vehicle power system 322 may regulate the charging and the power output of the battery to various electric circuits and the loads of the vehicle 106, as described above. When the vehicle 106 is a hybrid vehicle or an autonomous vehicle, the vehicle power system 322 may provide the required voltage for all of the components and enable the vehicle 106 to utilize the battery 320 power for a sufficient amount of time. In accordance with an embodiment, the vehicle power system 322 may correspond to power electronics, and may include a microcontroller that may be communicatively coupled (shown by dotted lines) to the in-vehicle network 126. In such an embodiment, the microcontroller may receive command from the powertrain control system 306 under the control of the microprocessor 302a.

In operation, the one or more vehicle sensors of the sensing system 308 may detect various vehicle parameters, such as a motion status, location information, a steering angle, a yaw rate, a speed value, and/or a rate of change of speed of the vehicle 106. The vehicle parameters may also include vehicle positional accuracy data, a brake system status of the braking system 314, a status of a vehicle stability system, vehicle diagnostics data, and/or other vehicle parameters of the vehicle 106. The vehicle data that corresponds to the detected vehicle parameters may be communicated to the processor 222 of the device 102, via the in-vehicle network 126, as the second set of input values. The second set of input values may be extracted by the processor 222 from the in-vehicle network 126, by use of the communication interface 228.

In accordance with an embodiment, the one or more ECUs, such as the body control module 304 and/or the powertrain control system 306, of the vehicle 106 may receive one or more control commands from the processor 222, via the in-vehicle network 126, such as the CAN bus. The control of the one or more functions of the vehicle 106 may be performed in response to the received one or more control commands from the processor 222. The receipt of the one or more control commands from the processor 222, to control the one or more functions of the vehicle 106, may be in accordance with the determined operating mode of the device 102. For example, when the determined operating mode is the about-to-drive mode 212, the one or more ECUs of the vehicle 106 may receive control command to generate an audio, visual, or a haptic response at the vehicle 106, to indicate a failure of user authentication, such as authentication of the first user 128.

In accordance with an embodiment, the control commands may be received by the one or more ECUs of the vehicle 106, to open or not to open a door of the vehicle 106 in the about-to-drive mode 212. Further, the control commands may be received by the one or more ECUs of the vehicle 106, to enable or disable the ignition by an ignition system of the vehicle 106 to start the vehicle 106 in the about-to-drive mode 212.

In accordance with an embodiment, the one or more ECUs of the vehicle 106 may receive control commands for dynamic configuration of the pre-defined personalization settings associated with the first user 128. The dynamic configuration may correspond to mechanical or non-mechanical configuration at the vehicle 106, as described in FIG. 2B.

In accordance with an embodiment, the one or more ECUs, such as the ECU 302, of the vehicle 106 may receive a control command to output vehicle and/or user fit-to-drive or not fit-to-drive status at the vehicle 106. Such a control command may be received when the device 102 is in the about-to-drive mode 212. The output may be a visual, audio or haptic output performed by use of the I/O device 226 of the device 102, the audio interface 316, the display 318, and/or indicator lights (such as light-emitting diode (LED) indicators) of the vehicle 106. In accordance with an embodiment, the device 102 may be powered by the battery 320 by use of the vehicle power system 322 of the vehicle 106. In accordance with an embodiment, the device 102 may be powered by a separate in-built battery.

In accordance with an embodiment, the one or more ECUs, such as the ECU 302, of the vehicle 106 may receive one or more temperature change signals at pre-defined time intervals when an authenticated user, such as the first user 128, is detected inside the vehicle 106. Such one or more temperature change signals may be received when the device 102 is in the outside driving mode 214.

In accordance with an embodiment, the wireless communication system 310 may receive a control command to communicate a theft alert to a communication device, such as the communication device 110, situated at the police control room 112. The control command may be received when the device 102 is in the outside driving mode 214. In accordance with an embodiment, the wireless communication system 310 may receive one or more control commands to communicate a health alert notification to the one or more external devices. The one or more control commands to communicate the health alert notification may be received when the operating mode of the device 102 is the outside driving mode 214 or the user-critical health mode 220.

In accordance with an embodiment, the one or more ECUs, such as the ECU 302 of the vehicle 106, may receive a temperature change signal from the device 102, to control temperature inside the vehicle 106. In this case, the temperature change signal may be received based on the body temperature of the first user 128 when the first user 128 is outside the vehicle 106, as detected by the device 102 in the outside non-driving mode 216.

In accordance with an embodiment, the wireless communication system 310 may receive a control command to communicate vehicle breakdown information of the vehicle 106 to the vehicle breakdown service provider 120, as instructed by the device 102. The control command to communicate the vehicle breakdown information may be received when the device 102 is in the vehicle-breakdown mode 218. In accordance with an embodiment, the wireless communication system 310 may receive a confirmation response from the vehicle breakdown service provider 120, via the second communication network 124.

Figure 4A:
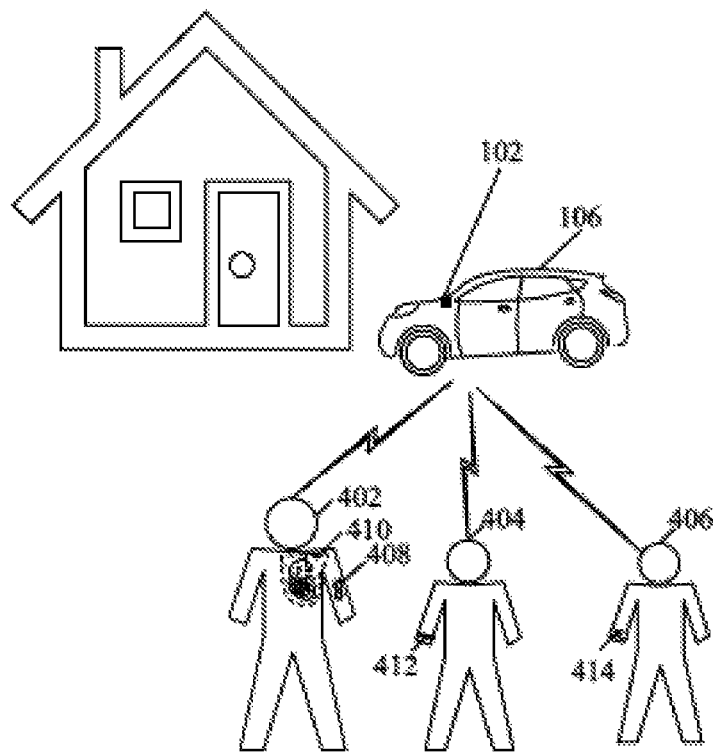
FIGS. 4A and 4B collectively illustrate a first exemplary scenario for implementation of the disclosed device and method to manage interaction with one or more control circuits in a vehicle and one or more wearable devices, in accordance with an embodiment of the disclosure.
Figure 4B:
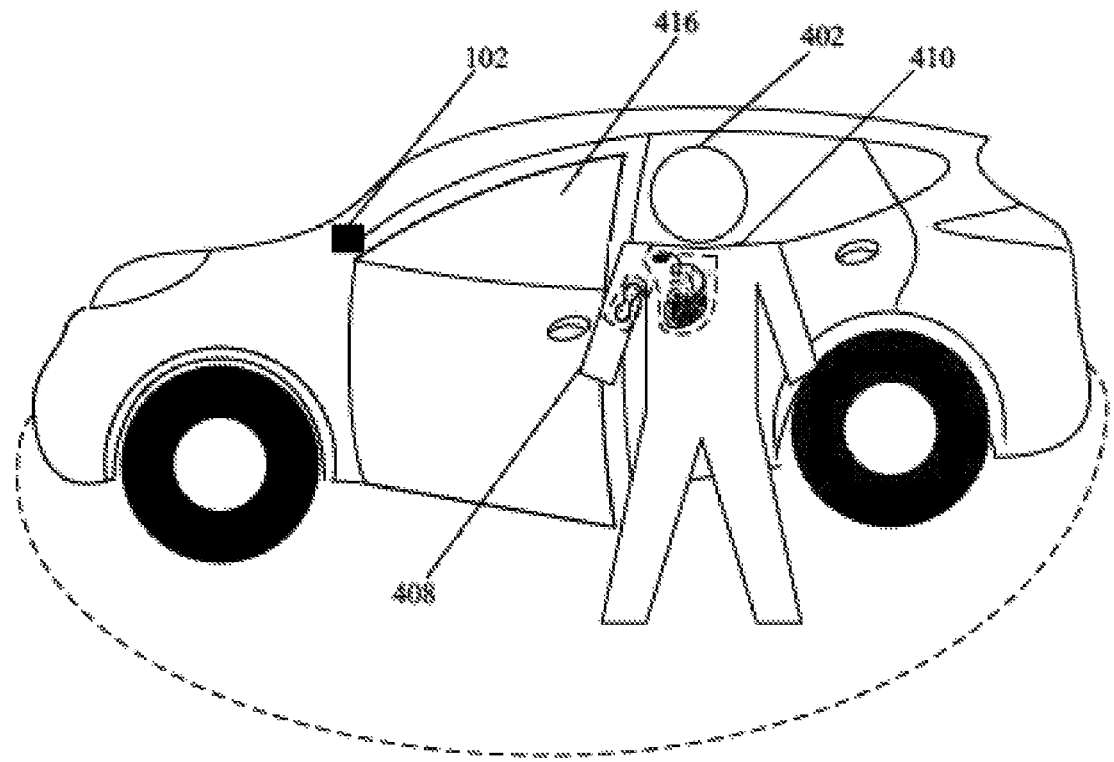

FIGS. 4A and 4B collectively illustrate a first exemplary scenario for implementation of the disclosed device and method to manage interaction with one or more control circuits in a vehicle and one or more wearable devices, in accordance with an embodiment of the disclosure. FIGS. 4A and 4B are explained in conjunction with elements from FIGS. 1, 2A, 2B, and 3. With reference to FIG. 4A, there is shown the vehicle 106, which may be parked at a parking lot of a home. The vehicle 106 may include the device 102 installed in the vehicle 106, and may be associated with multiple users of the vehicle 106, such as a first vehicle user 402, a second vehicle user 404, and/or a third vehicle user 406. There is further shown an iontophoresis patch 408 adhered to the arm of the first vehicle user 402 and an implantable cardioverter-defibrillator (ICD) 410 implanted into the first vehicle user 402. There is also shown a smart-band 412 worn by the second vehicle user 404, and a smart-watch 414 worn by the third vehicle user 406.

In accordance with the first exemplary scenario, the iontophoresis patch 408, the ICD 410, the smart-band 412, and the smart-watch 414 may correspond to the one or more wearable devices 104 (FIG. 1). The wearable devices of the first vehicle user 402, the second vehicle user 404, and the third vehicle user 406 may be pre-registered at the device 102. In accordance with an embodiment, the first vehicle user 402 may be a head of the family that may pre-define the wearable devices, such as the iontophoresis patch 408, and cardioverter-defibrillator (ICD) 410, associated with the first vehicle user 402, as wearable devices of a "Master User", at the device 102. The first vehicle user 402 may also pre-define user levels of the wearable devices associated with other family members, such as the second vehicle user 404 and the third vehicle user 406. For example, the smart-band 412 worn by the second vehicle user 404 may be pre-defined as wearable device of, "User Level: <Level 2>". Various settings, such as speed limit of 70 Km/Hour for the vehicle 106, may be defined for the second vehicle user 404 of user level, "<Level 2>". Valid vital physiological parameters of the second vehicle user 404 may be received from the smart-band 412, worn by the second vehicle user 404 at the time of registration of the smart-band 412, at the device 102. Such vital physiological parameters received at the time of registration of the wearable device, such as the smart-band 412, may be stored at the device 102 or a remote server, such as the cloud server 114. This information may be used later during user authentication. Similarly, the smart-watch 414 worn by the third vehicle user 406 may be pre-defined as wearable device of, "User Level: <Level 3>". A speed limit of "60 km/hr" for the vehicle 106 may be defined for the third vehicle user 406 of user level, "<Level 3>", at the device 102.

In operation, the device 102 may be configured to receive input values from the wearable devices, such as the iontophoresis patch 408, the ICD 410, the smart-band 412, and the smart-watch 414, communicatively coupled to the device 102. The device 102 may be configured to receive input values from one or more vehicle sensors, such as a GPS sensor, embedded in vehicle 106 or the device 102. The device 102 may be configured to determine an operating mode of the device 102 as the home mode 210, based on the received input values from the wearable devices and the input values received from one or more vehicle sensors.

In accordance with an embodiment, the device 102 may be configured to continuously and simultaneously monitor vital health data of multiple users, such as the first vehicle user 402, the second vehicle user 404, and the third vehicle user 406, based on the received input values from the wearable devices, such as the iontophoresis patch 408, the ICD 410, the smart-band 412, and the smart-watch 414. The device 102 may be configured to detect whether received vital health data of the first vehicle user 402, the second vehicle user 404, and the third vehicle user 406, is within normal limits and/or in accordance with preset health thresholds (such as personalized health thresholds based on vital heath data of a user) that corresponds to each of the users. In instances when a normal heath condition is detected, the device 102 may continue to monitor vital health data of the multiple users. In instances, when an abnormal heath condition is detected for the first vehicle user 402 or the second vehicle user 404, the device 102 may switch the operating mode to a user-critical health mode 220. The device 102 may send a health alert notification with current location information, such as home location, of the master user, such as the first vehicle user 402, to a pre-defined caregiver of the family members.

In accordance with an embodiment, at least one of the multiple users, such as the first vehicle user 402, may want to visit a friend and may move towards the vehicle 106 that includes the device 102. The device 102 may detect that the iontophoresis patch 408 and the ICD 410 of the first vehicle user 402 are within a pre-defined first proximity range of the device 102 or the vehicle 106, such as within a range of one meter from the device 102. The device 102 may then switch the operating mode from the home mode 210 to the about-to-drive mode 212.

With reference to FIG. 4B, there is further shown a vehicle door 416, the device 102 installed in the vehicle 106 that may be parked at a parking lot of a home, and the first vehicle user 402 in a vicinity of the vehicle 106. The device 102 may be configured to perform authentication of one or more users, such as the first vehicle user 402, the second vehicle user 404, and/or the third vehicle user 406, when at least a wearable device that corresponds to an associated user is detected within a pre-defined first proximity range of the device 102. For example, when the iontophoresis patch 408 and the ICD 410 are detected with the proximity range of "1 meter" from the device 102, the device 102 may retrieve the input values from the ICD 410 and/or the iontophoresis patch 408 associated with the first vehicle user 402. The retrieved input values in this case may be vital physiological parameters (such as heart rate), gender of patient, unique identifier of the wearable device (such as the ICD 410), and/or ECG data. The received input values may be validated based on a comparison with the pre-stored vital physiological parameters received at the time of registration of the ICD 410 at the device 102. In accordance with an embodiment, the received input values may be sent to the cloud server 114 to validate the received data for the user authentication of the first vehicle user 402.

In accordance with an embodiment, based on the authentication of the first vehicle user 402, the device 102 may send one or more control commands to the ECUs of the vehicle 106, to perform multiple functions at the vehicle 106. The device 102 may send one or more control commands to the ECUs, such as the body control module 304 and the powertrain control system 306 of the vehicle 106, to open the vehicle door 416, and to enable ignition by an ignition system of the vehicle 106. The device 102 may further send one or more control commands to the ECUs of the vehicle 106, to dynamically configure pre-defined personalization settings associated with the first vehicle user 402, authenticated at the vehicle 106. For example, certain mechanical configurations, such as adjustment of a driver seat of the vehicle 106 and adjustment of a position of a mirror of the vehicle 106, may be performed at the vehicle 106 based on the authentication of the first vehicle user 402. Similarly, non-mechanical configurations, such as auto-adjustment of vehicle internal ambience, auto-loading of songs playback list in accordance to preferences of the first vehicle user 402, may be performed at the vehicle 106.

In accordance with an embodiment, instead of the first vehicle user 402, the second vehicle user 404 may wish to drive and move towards the vehicle 106. The device 102 may then detect that the smart-band 412 of the second vehicle user 404, within the pre-defined first proximity range of the device 102. As described above for the first vehicle user 402, the device 102 may be configured to perform authentication of the second vehicle user 404, based on input values, such as the ECG data of the second vehicle user 404, received from the smart-band 412.

In certain instances, the wearable devices of the multiple users, such as the first vehicle user 402, the second vehicle user 404 and the third vehicle user 406, may be simultaneously detected within the pre-defined first proximity range of the device 102. In such instances, the device 102 may be configured to prioritize the master user, such as the first vehicle user 402. Consequently, the authentication and/or the dynamic configuration of the pre-defined personalization settings, may be performed for the master user, such as the first vehicle user 402 (in this case).

In accordance with an embodiment, when the multiple users are detected, the device 102 may activate one or more sensors, such as an ORVM camera, at the vehicle 106. The one or more sensors may determine a position of each user with respect to the vehicle 106 to detect entry point of each user to the vehicle 106. For example, the first vehicle user 402 may be detected to enter the vehicle 106 from the vehicle door 416 (such as driver-side vehicle door). The second vehicle user 404 may be detected to enter the vehicle 106 from another front vehicle door (such as the passenger side) of the vehicle 106. The third vehicle user 406 may be detected to enter the vehicle 106 from one of the rear doors of the vehicle 106.

In such instances, the device 102 may be configured to send a series of control commands to the ECUs of the vehicle 106 to dynamically configure pre-defined personalization settings associated with the multiple users authenticated at the vehicle 106. For example, the driver seat may be adjusted per the personalization settings of the first vehicle user 402. The front passenger side seat may be simultaneously adjusted per the personalization settings of the second vehicle user 404, and the rear passenger seat may be adjusted per the personalization settings of the third vehicle user 406. Other mechanical or non-mechanical configurations, such as the mirror adjustment and/or the internal temperature of the vehicle 106 may be adjusted per the personalization settings of the master user preset at the device 102. In instances when the master user is not present within the vehicle 106, the personalization settings of a user detected at the driver's seat may be used for the dynamically configuration at the vehicle 106.

In accordance with an embodiment, the device 102 may be configured to determine vehicle health by use of an on-board diagnostics (OBD) interface of the vehicle 106 before start of a drive. When both the user's health, such as of the first vehicle user 402, and the vehicle health is determined to be in satisfactory condition, an audio output may be generated to indicate that both the first vehicle user 402 and the vehicle 106 are fit to drive. The device 102 may be configured to switch an operating mode from the about-to-drive mode 212 to the outside driving mode 214.

In accordance with an embodiment, the device 102 may be configured to communicate with the wearable devices, such as the ICD 410, at pre-defined time interval when vehicle 106 is in motion and in the outside driving mode 214. This is done to confirm the presence of at least one authenticated user, such as the first vehicle user 402. When no authenticated user is detected in the vehicle 106 while in the outside driving mode 214, a theft alert may be communicated to the communication device 110, which may be situated at a police station, such as the police control room 112. The communication device 110 of the police control room 112 may be selected as the distance of the police control room 112 from the current location of the vehicle 106 may be the closest as compared to other police stations.

In accordance with an embodiment, the device 102 may be configured to control vehicle speed of the vehicle 106, based on the pre-defined user level of the authenticated user who drives the vehicle 106. For example, when the first vehicle user 402 (the master user) drives the vehicle 106, the device 102 may not control the speed limit of the vehicle 106. However, when the second vehicle user 404 of "<Level 2>" drives the vehicle 106, the device 102 may send a control command to the powertrain control system 306 to control the speed of the vehicle 106 to the pre-defined speed limit, such as "70 km/hr". Similarly, when the third vehicle user 406 of "<Level 3>" drives the vehicle 106, the device 102 may send a control command to the powertrain control system 306 to control the speed of the vehicle 106 to the pre-defined speed limit, such as "60 km/hr".

Figure 5:
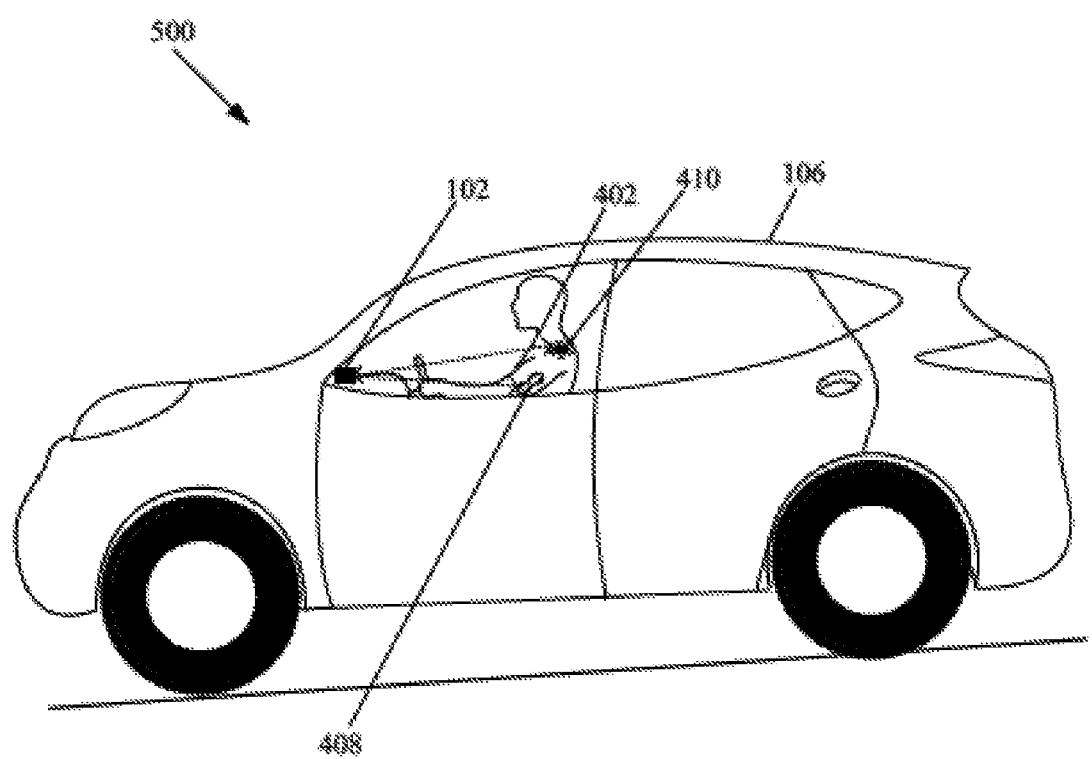
FIG. 5 illustrates a second exemplary scenario for implementation of the disclosed device and method to manage interaction with one or more control circuits in a vehicle and one or more wearable devices, in accordance with an embodiment of the disclosure.

FIG. 5 illustrates a second exemplary scenario for implementation of the disclosed device and method to manage interaction with one or more control circuits in a vehicle and one or more wearable devices, in accordance with an embodiment of the disclosure. FIG. 5 is explained in conjunction with elements from FIGS. 1, 2A, 2B, 3, 4A, and 4B. With reference to FIG. 5, there is shown a side view 500 of the vehicle 106 that depicts the first vehicle user 402 driving the vehicle 106. There is further shown the iontophoresis patch 408 and the ICD 410 of the first vehicle user 402 that are communicatively coupled to the device 102, used in the vehicle 106.

In operation, the device 102 may be configured to receive input values from the iontophoresis patch 408 and the ICD 410, which may be communicatively coupled to the device 102. The device 102 may be configured to receive input values from one or more vehicle sensors, such as the GPS sensor and the odometric sensors, embedded in vehicle 106. The device 102 may be configured to determine an operating mode of the device 102 as the outside driving mode 214, based on the received input values from the wearable devices, such as the iontophoresis patch 408 and the ICD 410, and the input values received from one or more vehicle sensors.

In accordance with an embodiment, the device 102 may be configured to detect an abnormal medical condition, such as ventricular tachycardia, in first vehicle user 402, based on the input values, such as high heartbeat rate and/or cardiac rhythm values, periodically received from the ICD 410. The device 102 may determine a severity level of the detected ventricular tachycardia to be critical for the first vehicle user 402, based on a health threshold associated with first vehicle user 402. The device 102 may then switch the operating mode from the outside driving mode 214 to the user-critical health mode 220.

In accordance with an embodiment, the device 102 in the user-critical health mode 220 may be configured to send a health alert notification with current location information of the first user 128 to the mobile device 108 of the caregiver 132, a nearest hospital, and/or an ambulance service provider, such as the ambulance service provider 118. When the device 102 detects that the ability to drive the vehicle 106 is impaired due to an abnormal medical condition of the first vehicle user 402, the device 102 may then send a control command to one or more ECUs of the vehicle 106 to switch the vehicle 106 to the autonomous mode. The vehicle 106 may then be steered automatically to drive the vehicle 106 to the nearest hospital.

In accordance with an embodiment, the device 102 may be configured to receive an input for the communication of the health alert to the mobile device 108 of the caregiver 132. The input may also correspond to a customized message from the first vehicle user 402. For example, the first vehicle user 402 may experience severe pain, such as an acute post-operative pain, and may want to communicate the customized message to inform the caregiver 132 of the pain. In accordance with an embodiment, the input that corresponds to the health alert and/or the customized message, may be provided by the first vehicle user 402 directly by use of the I/O device 226 (of the device 102). In accordance with an embodiment, the input may be a touch input provided by the first vehicle user 402, by use of the display 318. Further, the input may be a voice input provided by the first vehicle user 402, by use of the microphone attached to the audio interface 316 of the vehicle 106. Based on the received input, the device 102 may be configured to communicate the health alert with the customized message to indicate severe pain experienced by the first vehicle user 402 to the mobile device 108 of the caregiver 132, while the operating mode of the device 102 is the outside driving mode 214.

In accordance with an embodiment, the device 102 may be configured to receive instructions from the caregiver 132, for remote pain management of the first vehicle user 402. For example, the instruction from the mobile device 108 may be received in a pre-defined format, such as, "<release>Drug Name</release>; <duration>N seconds</duration>; <dosage>quantity</dosage>; <date_and_time>08-08-2015: 1800-1830</date_and_time>; <device_unique_ID>WD02</device_uniqueID>". The device 102 may perform parsing of the received instruction to send a controlled drug release command to a particular wearable device based on the received instructions, such as based on the unique identifier, such as "WD02", that refers to the iontophoresis patch 408. The controlled drug release command may comprise the instructions, such as "Release the pain relieving drug for 5 seconds", received from the caregiver 132. The iontophoresis patch 408 may release the drug for transdermal delivery of the drug, based on the received instructions. In accordance with an embodiment, consent from the first vehicle user 402 may be received by the device 102 or one of the wearable device associated with the first vehicle user 402, before administration of the drug in accordance with the instructions of the caregiver 132. Thus, a smart mechanism may be provided to interface between the wearable devices and the vehicle 106, to maximize usability of the wearable devices, ensure safety of the vehicle user, such as the first vehicle user 402, to provide enhanced healthcare on-the-go.

FIGS. 6A, 6B, 6C, 6D, 6E, 6F, and 6G collectively depict a flow chart that illustrates an exemplary method to manage interaction with one or more control circuits in a vehicle and one or more wearable devices, in accordance with an embodiment of the disclosure. With reference to FIGS. 6A to 6G, there is shown a flow chart 600. The flow chart 600 is described in conjunction with FIGS. 1, 2A, 2B, 3, 4, and 5. The method starts at step 601 and proceeds to step 602.

At step 602, a first set of input values may be received from the one or more wearable devices 104 (FIG. 1). The one or more wearable devices 104, such as the iontophoresis patch 408 and the ICD 410, may be associated with the first user 128, such as the first vehicle user 402 (FIG. 4A). The one or more wearable devices 104 may be communicatively coupled to the device 102, used in the vehicle 106, via the first communication network 122. In accordance with an embodiment, the first set of input values may comprise vital health data, such as the ECG, heart rate, respiratory rate, blood oxygen level, blood alcohol level, blood pressure, and/or body temperature of the first user 128 (as described in detail FIGS. 2A and 2B).

At step 603, a second set of input values may be received from the one or more vehicle sensors embedded in the vehicle 106. For example, the second set of input values may be sent from one or more sensors of the sensing system 308, vehicle power system 322, powertrain control system 306 or body control module 304. The second set of input values may comprise vehicle data, such as the motion status, the geospatial position, yaw rate, speed, direction of travel, steering angle, a driving operation mode and/or other vehicle parameters of the vehicle 106, which can be sent from the sensing system 308, vehicle power system 322, powertrain control system 306, ECU 302 or body control module 304 via in-vehicle network 126. The driving operation mode may be one of: (1) a manual driving mode for which a driver drives the vehicle 106 manually, (2) an autonomous driving mode in which the vehicle 106 drives automatically, and (3) an emergency driving mode in which the vehicle 106 automatically sets a destination without the passenger's input and drives automatically. In addition to the second set of input values, image data or video data captured by sensors of the sensing system 308, such as one or more cameras, millimetre-wave scanner, may also be received. The image data or the video data may include an image of outside environment of the vehicle 106 or an image of driver or passenger of the vehicle 106. The second set of input values may comprise a result of analysis of the image data or the video data, such as a name of an identified object in the image data or the video data, a feeling of the passenger, a climate of the outside environment, and a level of an accidental risk of the vehicle 106 considering outside environment. In accordance with an embodiment, step 603 may be processed in parallel to step 602.

At step 604, a data type of the received first set of input values and the second set of input values may be determined. The data type of the first set of input values may correspond to heath data of vehicle users, such as the first user 128 (FIG. 1), the first vehicle user 402, second vehicle user 404, and/or the third vehicle user 406 (FIG. 4A). The data type of the second set of input values may correspond to heath data, such as the motion status and/or current status of the vehicle stability system, of the vehicle 106.

At step 605, an operating mode of the device 102 may be determined, based on the received first set of input values and the second set of input values. In accordance with an embodiment, a current location information of the vehicle 106, a motion status of the vehicle 106, and/or the determined data type may be utilized for the determination of the operating mode. In accordance with an embodiment, one or more functions of the vehicle 106 may be controlled based on the determined operating mode of the device 102. The determined operating modes may be the home mode 210, the about-to-drive mode 212, the outside driving mode 214, the outside non-driving mode 216, the vehicle-breakdown mode 218, and/or the user-critical health mode 220, as described in FIG. 2A. In accordance with an embodiment, the control of the one or more functions of the vehicle 106 may be further based on the determined data type and one or more pre-configured user-settings associated with the first user 128.

Figure 6A:
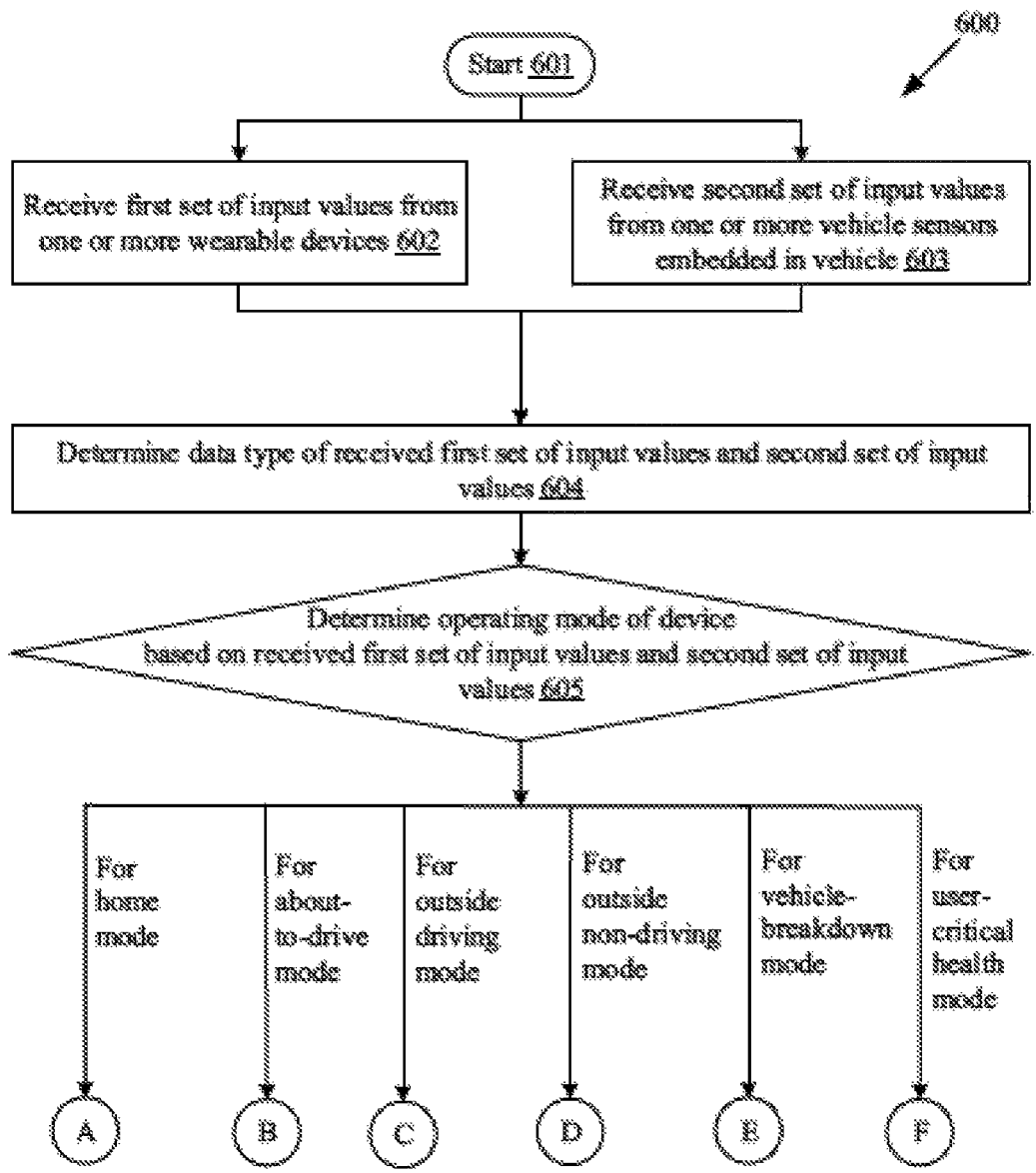
FIGS. 6A, 6B, 6C, 6D, 6E, 6F, and 6G collectively depict a flow chart that illustrates an exemplary method to manage interaction with one or more control circuits in a vehicle and one or more wearable devices, in accordance with an embodiment of the disclosure.
Figure 6B:
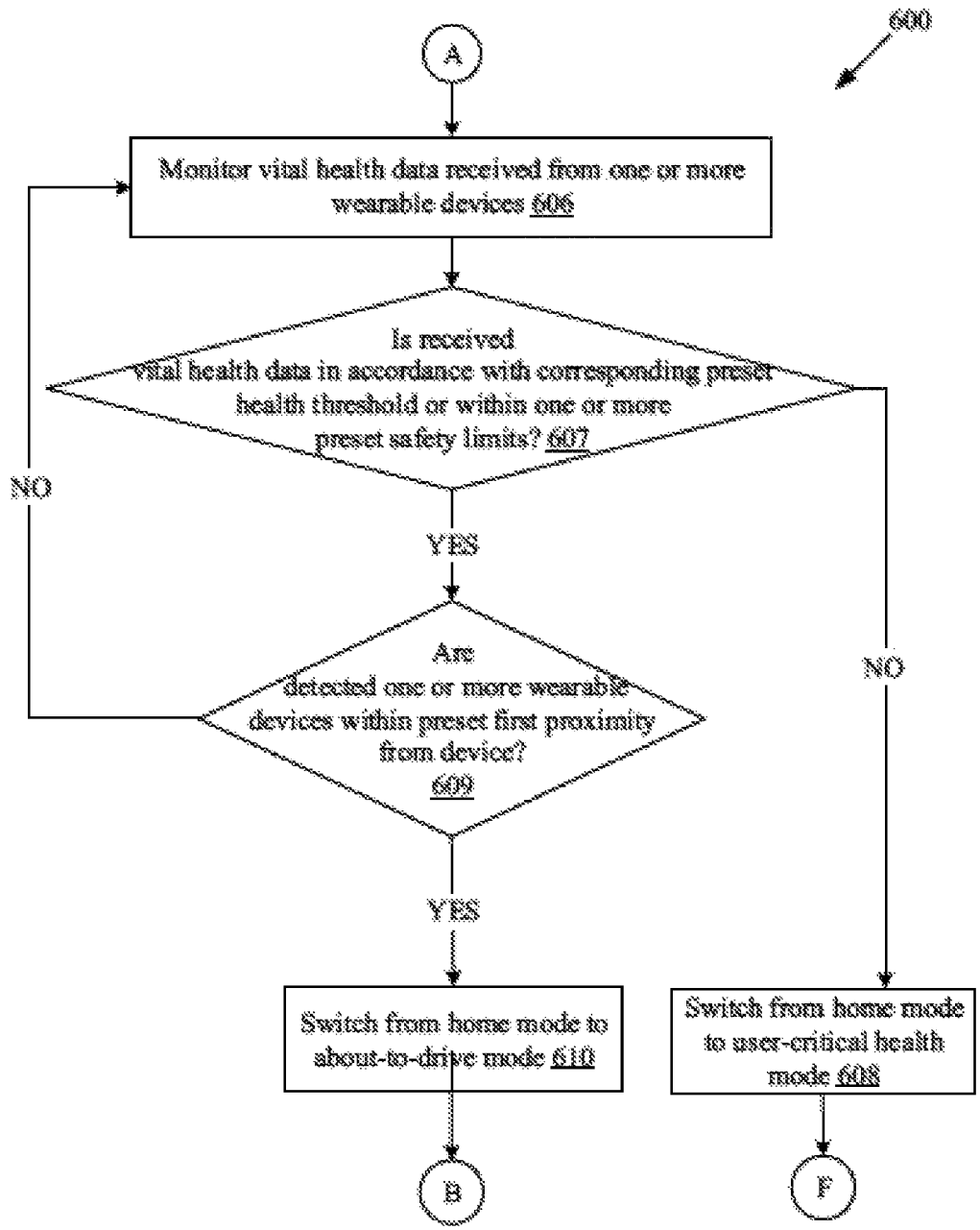
Figure 6C:
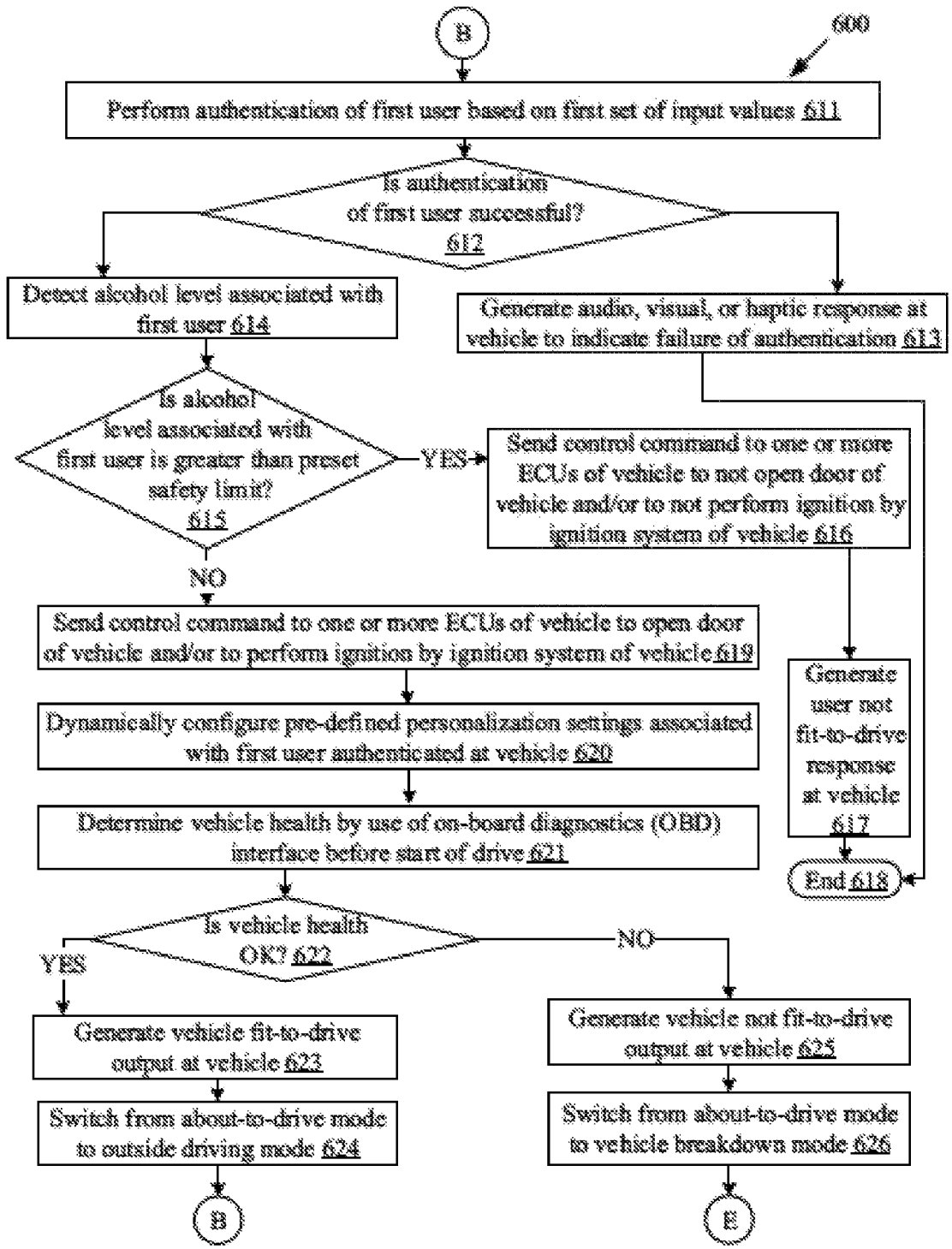
Figure 6D:
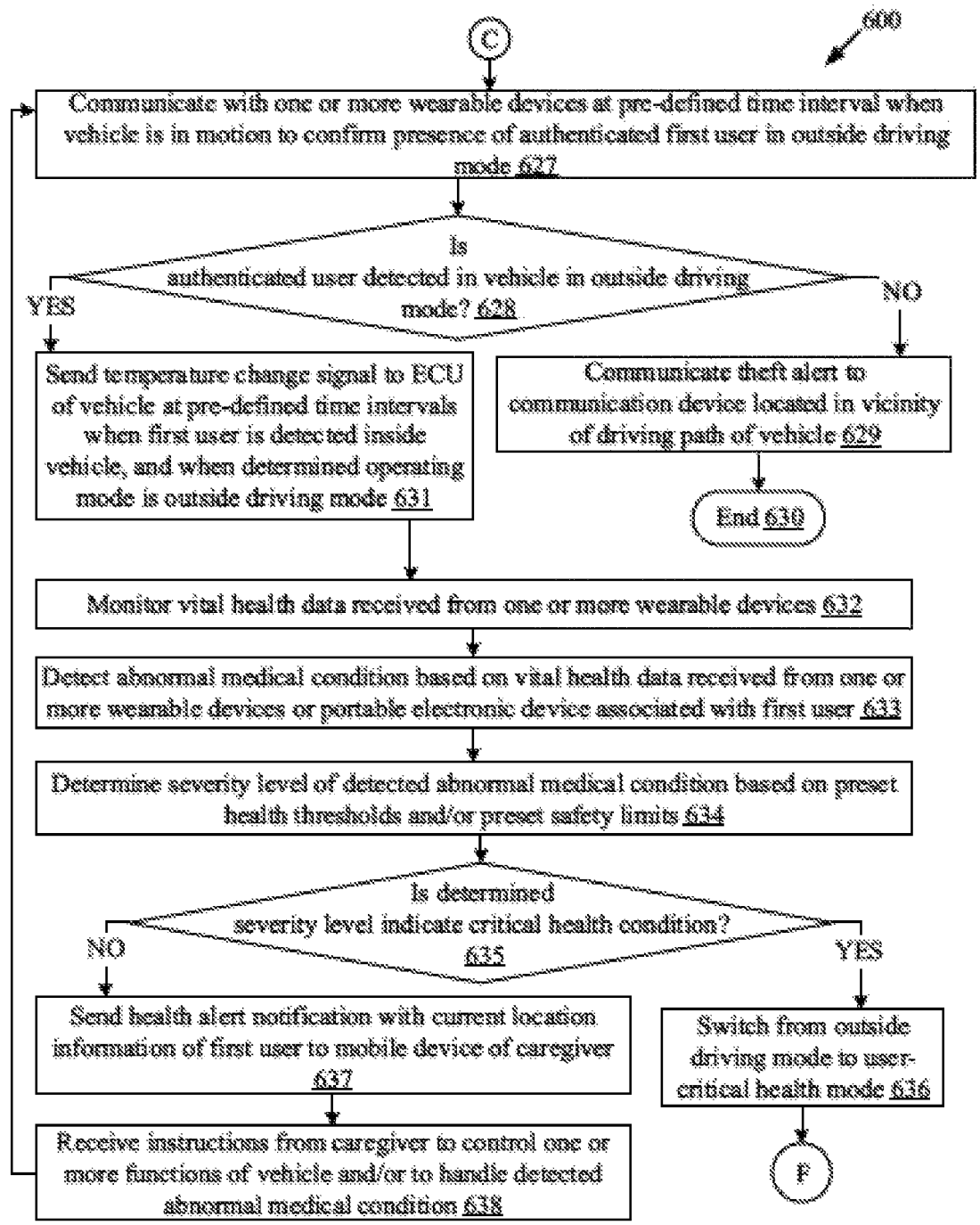
Figure 6E:
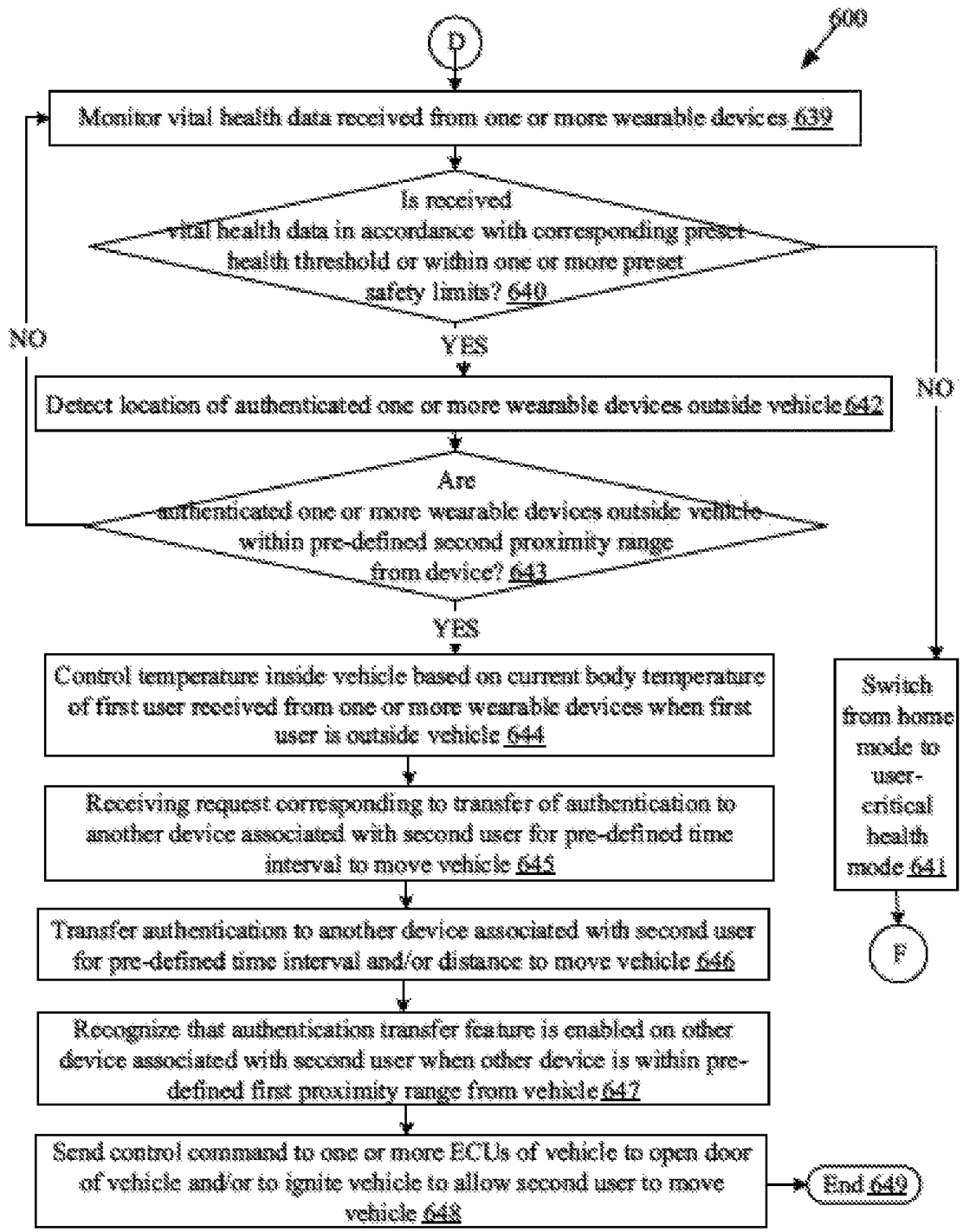
Figure 6F:
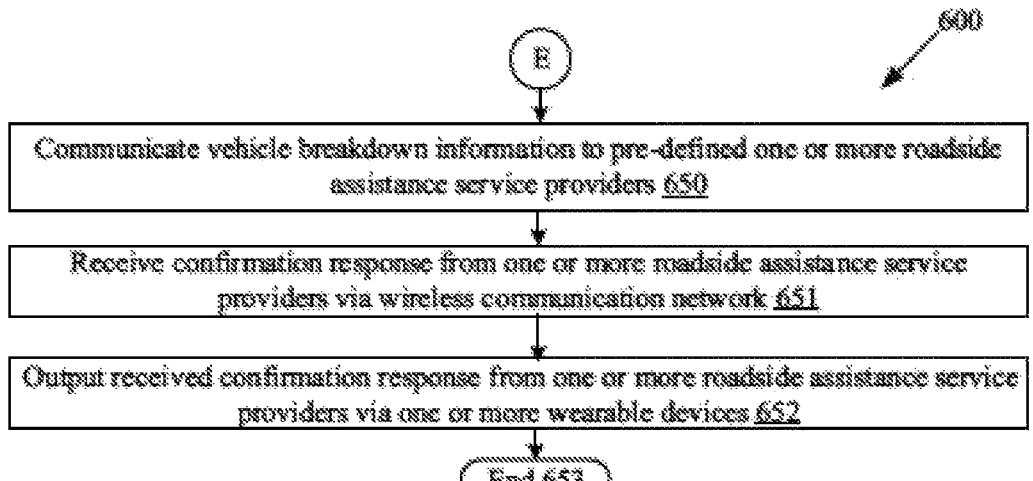
Figure 6G:
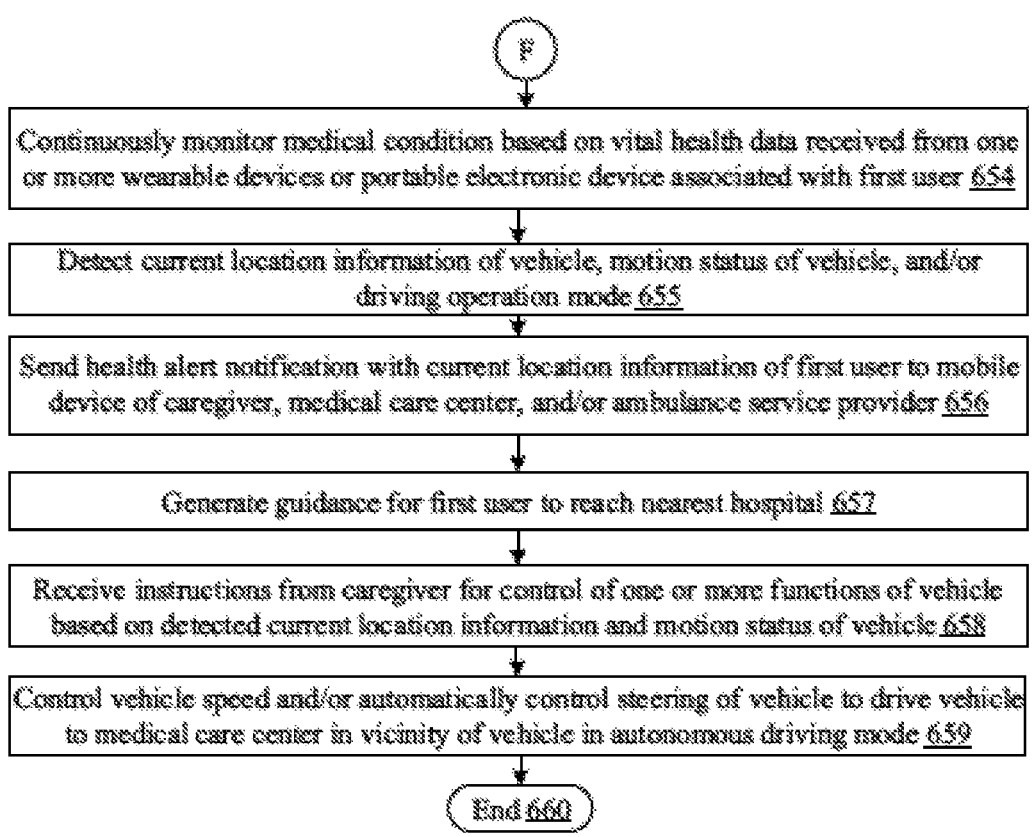

In an instance when the determined operating mode is the home mode 210, the control passes to step 606 (FIG. 6B). In an instance when the determined operating mode is the about-to-drive mode 212, the control passes to step 611 (FIG. 6C). In an instance when the determined operating mode is the outside driving mode 214, the control passes to step 627 (FIG. 6D). In an instance when the determined operating mode is the outside non-driving mode 216, the control passes to step 639 (FIG. 6E). In an instance when the determined operating mode is the vehicle-breakdown mode 218, the control passes to step 650 (FIG. 6F). In an instance when the determined operating mode is the user-critical health mode 220, the control passes to step 654 (FIG. 6G).

With reference to FIG. 6B, the control at step 606 may be received from step 605 (FIG. 6A), when the determined operating mode is the home mode 210. At step 606, vital health data, such as heart rate, received from the one or more wearable devices 104 may be monitored when the determined operating mode is the home mode 210 (shown and further described in FIG. 4A). At step 607, it may be detected whether the received vital health data is in accordance with a preset health threshold or within one or more preset medical safety limits, based on the corresponding vital health parameters, such as heart rate. In instances when the received vital health data not in accordance with preset health threshold and/or not within the one or more preset medical safety limits, the control passes to step 608. In instances when the received vital health data is in accordance with preset health threshold and/or within one or more preset medical safety limits, the control passes to step 609.

At step 608, the home mode 210 may be switched to the user-critical health mode 220 at the device 102. The control may pass to step 654 (FIG. 6G). At step 609, it may be detected whether the one or more wearable devices 104 are within preset first proximity range from the device 102. For example, as shown and described in FIG. 4B, the device 102 may detect that the iontophoresis patch 408 and the ICD 410 of the first vehicle user 402 are within a pre-defined first proximity range of the device 102 or the vehicle 106, such as within a range of one meter from the device 102.

In instances when the one or more wearable devices 104 are within the preset first proximity range from the device 102, the control passes to step 610. In instances when the one or more wearable devices 104 are not within the preset first proximity range from the device 102, the control may pass back to step 606. At step 610, the home mode 210 may be switched to the about-to-drive mode 212 at the device 102. The control may then pass to step 611 (FIG. 6C).

With reference to FIG. 6C, the control at step 611 may be received from step 605 (FIG. 6A), when the determined operating mode is the about-to-drive mode 212. At step 611, authentication of the first user 128 may be performed, based on the first set of input vales received from the one or more wearable devices 104 associated with the first user 128. The authentication may be performed when the one or more wearable devices 104, associated with the first user 128, are detected within the preset proximity range from the device 102 used in the vehicle 106. An example of the authentication of the first vehicle user 402 within the preset proximity range, such as "1 meter" from the device 102, is shown and described in FIG. 4B.

At step 612, it may be confirmed whether the authentication of the first user 128 is successful or unsuccessful. In instances when the authentication is unsuccessful, the control may pass to step 613. In instances when the authentication is successful, the control may pass to step 614. At step 613, an audio, visual, or a haptic response may be generated at the vehicle 106. This is done to indicate the failed authentication. The control may pass back to step 611 for another attempt of the authentication or may pass to the end step 618 (FIG. 6C). At step 614, it may be detected whether an alcohol level associated with the first user 128 is greater than a preset safety limit that corresponds to the blood alcohol content (BAC). In instances when the alcohol level (such as an intoxication level of alcohol) associated with the first user 128 is greater than the preset safety limit, the control passes to step 616. In instances when the alcohol level associated with the first user 128 is less than the preset safety limit, the control passes to step 619.

At step 616, one or more control commands may be sent to one or more ECUs, such as the body control module 304 and/or the powertrain control system 306, of the vehicle 106 to not open door of vehicle 106 and/or to not perform ignition by the ignition system of the vehicle 106. This may help to avoid a traffic rule violation and prevent the first user 128 to drive the vehicle 106 when a high BAC is detected. At step 617, a user, such as the first user 128, not fit-to-drive response may be generated at the vehicle 106. The response may be an audio or a visual response at the vehicle 106. The control may pass to the end step 618 of FIG. 6C.

At step 619, when the alcohol level associated with the first user 128 is less than the preset safety limit, one or more control commands may be sent to one or more ECUs, such as the body control module 304 and/or the powertrain control system 306, of the vehicle 106 to open the door of the vehicle 106 and/or to perform ignition by the ignition system of the vehicle 106 to start the vehicle 106. At step 620, pre-defined personalization settings associated with the first user 128, authenticated at the vehicle 106, may be dynamically configured. Such dynamic configurations that may include both the mechanical and non-mechanical configurations may occur when the authentication of the first user 128 is successful, as exemplified previously in FIGS. 2B and 4B.

At step 621, vehicle health, by use of an on-board diagnostics (OBD) interface, may be determined for the vehicle 106 before start of a drive. At step 622, it may be checked to confirm whether the vehicle health is "OK" or faulty. In instances when the vehicle health is determined to be in normal condition, the control may pass to step 623. In instances when the vehicle health is determined to be faulty, the control may pass to step 625.

At step 623, a vehicle fit-to-drive output may be generated at the vehicle 106. The output may be a visual output, such as a green light indicator, a haptic output, or an audio output at the vehicle 106. This may indicate that the vehicle 106 is fit to drive. At step 624, the about-to-drive mode 212 at the device 102 may be switched to the outside driving mode 214. The control may then pass to step 627 (FIG. 6D). In accordance with an embodiment, between step 622 and step 623, a feeling of the driver or passenger may be detected by the device 102. The detection may occur as the first set of input values and a driving operation mode currently set in the vehicle 106 as the second set of the input values are received by the device 102. Accordingly, an appropriate driving operation mode may be decided based on detected feeling and the currently set operation mode. The decided appropriate driving operation mode may be sent to the vehicle 106 so that an appropriate driving operation mode as per the detected feeling may be set at vehicle 106. For example, a feeling of the passenger may be detected as "irritated" and the currently set driving operation mode may be "autonomous driving mode". In such a case, "autonomous relaxing driving mode" which drives slower than usual may be selected by the device 102. Further, a sparse driving route may also be selected by the device 102. A command to set the "autonomous relaxing driving mode" may be sent to the vehicle 106 from the device 102.

At step 625, a vehicle not fit to drive output may be generated at the vehicle 106. The output may be another visual output, such as a red light indicator, a haptic output, or an audio output at the vehicle 106, to indicate that the vehicle 106 is not fit to drive. At step 626, the about-to-drive mode 212 at the device 102 may be switched to the vehicle-breakdown mode 218. The control may then pass to step 650 (FIG. 6F).

With reference to FIG. 6D, the control of step 627 may be received from step 605 (FIG. 6A) when the determined operating mode is the outside driving mode 214. At step 627, the device 102 may communicate with the one or more wearable devices 104 at a pre-defined time interval, such as every 20 seconds or every 5 minutes, while the vehicle is in motion. This may be done to confirm the presence of an authenticated user, such as the authenticated first user 128, in the outside driving mode 214, as shown in an example in FIG. 5. At step 628, while in the outside driving mode 214, it may be detected whether at least one authenticated user, such as the first user 128 (FIG. 1) or the first vehicle user 402 (FIG. 5), is present in the vehicle 106.

In instances when an authenticated user is not detected in the vehicle 106 in the outside driving mode 214, the control may pass to step 629. In instances when an authenticated user is detected in the vehicle 106 in the outside driving mode 214, the control may pass to step 631. At step 629, a theft alert may be communicated to a communication device, such as the communication device 110 situated at a police station, located within a vicinity of the vehicle 106. The control may pass to end step 630.

At step 631, while in the outside driving mode 214, one or more temperature change signals may be sent to an ECU of the vehicle 106 at pre-defined time intervals. This may occur when the authenticated user, such as the first user 128 or the first vehicle user 402, is detected inside the vehicle 106. At step 632, vital health data, such as the heart rate and/or blood pressure, received from the one or more wearable devices 104 may be monitored.

At step 633, an abnormal medical condition may be detected based on the vital health data received from the one or more wearable devices 104 or a portable electronic device associated with the authenticated user, such as the first user 128. For example, as described in FIG. 5, the device 102 may be configured to detect an abnormal medical condition, such as ventricular tachycardia, in first vehicle user 402, based on high heartbeat rate and/or cardiac rhythm values, periodically received from the ICD 410. At step 634, a severity level of the detected abnormal medical condition may be determined based on the preset health thresholds and/or the preset medical safety limits.

At step 635, the preset health thresholds and/or the preset medical safety limits may be used to ascertain whether the determined severity level indicates a critical health condition. In instances when the determined severity level indicates the critical health condition, the control may pass to the step 636. In instances when the determined severity level does not indicate the critical health condition, the control may pass to the step 637. At step 636, the outside driving mode 214 may be switched to the user-critical health mode 220 at the device 102. The control may then pass to step 654 in the user-critical health mode 220 (FIG. 6G).

At step 637, for the outside driving mode 214, a health alert notification with current location information of the first user may be sent to a mobile device, such as the mobile device 108, of the caregiver 132. At step 638, instructions may be received from the caregiver 132 to control one or more functions, such as temperature and humidity control, of the vehicle 106 and/or to remotely handle the detected abnormal medical condition. Examples of the instructions received in response to the health alert notification have been described previously in the FIG. 5. The control may then pass back to step 627 or step 632, per the pre-configured user settings at the device 102.

With reference to FIG. 6E, the control of step 639 may be received from step 605 (FIG. 6A) when the determined operating mode is the outside non-driving mode 216. At step 639, vital health data received from the one or more wearable devices 104 of the first user 128, may be monitored at the device 102. At step 640, it may be detected whether the received vital health data of the first user 128 is in accordance with the preset health threshold that corresponds to the first user 128 and/or the preset medical safety limits.

In instances when the received vital health data is not in accordance with the preset health threshold and/or not within one or more preset medical safety limits in the outside non-driving mode 216, the control passes to step 641. In instances when the received vital health data is below preset health threshold and/or within one or more preset medical safety limits in the outside non-driving mode 216, the control passes to step 642.

At step 641, the outside non-driving mode 216 may be switched to the user-critical health mode 220 at the device 102. The control may pass to step 654 (FIG. 6G). At step 642, location of the authenticated one or more wearable devices 104 outside the vehicle 106, may be detected. At step 643, it may be detected whether the one or more wearable devices 104, such as iontophoresis patch 408 and the ICD 410, are within a preset second proximity range, such as beyond the "1 meter" range, from the device 102. In instances when the one or more wearable devices 104 are not within the preset second proximity range from the device 102, the control may pass back to step 639. In instances when the one or more wearable devices 104 are detected within the preset second proximity range from the device 102, the control may pass to step 644.

At step 644, a temperature inside the vehicle 106 may be remotely controlled based on current body temperature of the first user 128, when the first user 128 is outside the vehicle 106 in the outside non-driving mode 216. The current body temperature of the first user 128 may be received from the one or more wearable devices 104 at the device 102. This may occur when the wearable devices 104 are detected within the second proximity range outside the vehicle 106. The device 102 may then send one or more commands to a suitable ECU of the vehicle 106 to set the temperature of the vehicle 106, per the current body temperature of first user 128. At step 645, a request may be received to transfer the authentication to another device associated with the second user 130, such as a valet, for a pre-defined time interval to permit movement of the vehicle 106.

At step 646, the authentication may be transferred to the other device associated with the second user 130 for the pre-defined time interval, to permit movement of the vehicle 106 in a pre-determined radial distance. The authentication may be transferred based on the request received from the one or more wearable devices 104 associated with the authenticated first user 128 in the outside non-driving mode 216. The transfer the authentication from the first user 128 to the second user 130, such as the valet, may be useful during valet parking of the vehicle 106. At step 647, the device 102 may recognize that an authentication transfer feature is enabled on other device associated with second user 130, when the other device is detected within the pre-defined first proximity range from the device 102 and/or the vehicle 106. The authentication transfer feature may be enabled at the other device, based on the transferred authentication from the device 102, or from at least one of the one or more wearable devices 104 of the first user 128.

At step 648, one or more control commands may be sent to one or more ECUs, such as the body control module 304, and/or the powertrain control system 306, of the vehicle 106. The one or more control commands may be sent to open the door of the vehicle 106 and/or to perform ignition by the ignition system of the vehicle 106, to allow the second user 130 to start and move the vehicle 106. The control may pass to the end step 649 of FIG. 6E.

With reference to FIG. 6F, the control of step 650 may be received from step 605 (FIG. 6A), when the determined operating mode is the vehicle-breakdown mode 218. At step 650, vehicle breakdown information may be communicated to one or more roadside assistance service providers, such as the vehicle breakdown service provider 120, pre-configured at the device 102.

At step 651, a confirmation response may be received at the device 102 from the one or more roadside assistance service providers (such as the vehicle breakdown service provider 120), via the second communication network 124. At step 652, output of the received confirmation response from the one or more roadside assistance service providers may occur via the device 102. In accordance with an embodiment, output of the received confirmation response may occur via the one or more wearable devices 104, associated with the first user 128, when the first user 128 is detected outside the vehicle 106. The control may pass to end step 653 of FIG. 6F.

With reference to FIG. 6G, the control of step 654 may be received from step 605 (FIG. 6A) when the determined operating mode is the user-critical health mode 220. At step 654, a medical condition of the first user 128 may be continuously monitored, based on the vital health data received from the one or more wearable devices 104 or the portable electronic device associated with the first user 128. At step 655, current location information of the vehicle 106 (and/or the device 102 used in the vehicle 106), a motion status of vehicle 106 and an operation mode may be detected.

At step 656, a health alert notification, with current location information of first user 128, may be sent to the mobile device 108 of the caregiver 132, the medical care center 116, and/or the ambulance service provider 118 in the user-critical health mode 220. At step 657, guidance information may be generated for the first user 128 to reach a nearest hospital from the detected current location of the first user 128 or the medical care center 116 pre-configured at the device 102.

At step 658, instructions may be received from the caregiver 132 for the control of the one or more functions of the vehicle 106, based on the detected current location information and the motion status of the vehicle 106. At step 659, in the user-critical health mode 220, vehicle speed may be controlled. In accordance with an embodiment, the vehicle 106 may be switched to an autonomous driving mode. The autonomous driving mode allows for the vehicle 106 to be automatically steered to a medical care center, such as the medical care center 116 or the hospital, within a vicinity of the vehicle 106. The control may pass to the end step 660 (FIG. 6G).

As an alternative step of the above step 656, the device 102 may send a command to the vehicle 106 so that the vehicle 106 sets an emergency driving mode as the driving operation mode. Such command may be sent to the vehicle 106 if the received driving operation mode of the vehicle 106 is not the emergency driving mode. Also, the device 102 may send location details of a nearest medical care centre 116 and a command to the vehicle 106 so that the vehicle 106 sets the location as destination of the current drive. Accordingly, the device 102 may send a command to cause the vehicle 106 to set the emergency driving mode and the destination based on the first set of input values and the second set of the input values.

In accordance with an embodiment of the disclosure, a device (such as the device 102 (FIG. 1)) to manage interaction with one or more control circuits in a vehicle (such as the vehicle 106 (FIG. 1)) and the one or more wearable devices 104 is disclosed. The device may comprise one or more circuits (hereafter referred to as the processor 222 (FIG. 2B)). The processor 222 may be configured to receive a first set of input values from the one or more wearable devices 104 (FIG. 1) communicatively coupled to the device used in the vehicle. The one or more wearable devices 104 may be associated with the first user 128. The processor 222 may be configured to receive a second set of input values from one or more vehicle sensors (such as vehicle sensors of the sensing system 308 (FIG. 3)) embedded in the vehicle. The processor 222 may be configured to determine an operating mode of the device, based on the received first set of input values and the received second set of input values. The processor 222 may be configured to control one or more functions of the vehicle, based on the determined operating mode of the device.

In accordance with an embodiment of the disclosure, a vehicle (such as the vehicle 106 (FIGS. 1 and 3)) is disclosed. The vehicle may comprise the battery 320 and an electronic control unit (such as the ECU 302 (FIG. 3)). The vehicle may further comprise a device (hereafter referred to as the device 102 (FIG. 1)), powered by the battery 320, configured to control communication between the one or more wearable devices 104, associated with the first user 128 and the electronic control unit of the vehicle. A first set of input values may be received by the device 102 from the one or more wearable devices 104, which are communicatively coupled to the device 102. The vehicle may further comprise one or more vehicle sensors (such as vehicle sensors of the sensing system 308 (FIG. 3)) embedded in the vehicle that may be configured to communicate a second set of input values to the device 102. The device 102 may be configured to determine an operating mode of the device 102, based on the received first set of input values and the received second set of input values. The device 102 may be configured to control one or more functions of the vehicle, based on the determined operating mode.

Various embodiments of the disclosure may provide a non-transitory computer readable medium and/or storage medium, with a set of computer-executable instructions stored thereon to cause a machine and/or a computer to manage interaction with one or more control circuits in a vehicle (such as the vehicle 106 (FIG. 1)) and the one or more wearable devices 104. The set of computer-executable instructions in a device, such as the device 102 (FIGS. 1, 2A, and 2B), may cause the machine and/or computer to perform the steps that comprise receipt of a first set of input values from the one or more wearable devices 104 communicatively coupled to the device used in the vehicle. The one or more wearable devices 104 may be associated with a first user, such as the first user 128. A second set of input values may be received from one or more vehicle sensors embedded in the vehicle. An operating mode of the device may be determined based on the received first set of input values and the second set of input values. One or more functions of the vehicle may be controlled based on the determined operating mode of the device.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features enabling the implementation of the methods described herein, and which when loaded in a computer system is able to carry out these methods. Computer program, in the present context, means any expression, in any language, code or notation, of a set of instructions intended to cause a system having an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A device for interaction management of a vehicle, said device comprising:
   circuitry configured to:
      receive a first set of input values from a plurality of wearable devices, wherein
         said plurality of wearable devices is communicatively coupled to said device,
         said plurality of wearable devices comprises a first wearable device associated with a first user of a plurality of users, and said first set of input values includes a specific value associated with health data of said first user;
receive a second set of input values from at least one vehicle sensor in said vehicle;
determine an operating mode of a plurality of operating modes of said device based on said first set of input values received from said plurality of wearable devices and said second set of input values received from said at least one vehicle sensor;
determine that said specific value is within a first threshold and a second threshold;
detect said first wearable device is within a first proximity range of said device subsequent to said determination that said specific value is within said first threshold and said second threshold;
authenticate said first user associated with said first wearable device based on:
said specific value associated with said health data of said first user; and
said detection that said first wearable device is within said first proximity range of said device;
receive a request from said first wearable device to transfer said authentication from said first wearable device to a second wearable device of said plurality of wearable devices, wherein
said second wearable device is associated with a second user of said plurality of users, and
said first wearable device is different from said second wearable device;
transfer said authentication to said second wearable device from said first wearable device for a specific time period based on said request;
detect said second wearable device is in a second proximity range of said vehicle;
recognize enablement of an authentication transfer feature on said second wearable device based on said detection of said second wearable device in said second proximity range of said vehicle, wherein said authentication transfer feature indicates said transferred authentication; and
control at least one function of said vehicle based on said recognition.

2. The device according to claim 1, wherein said circuitry is further configured to:
determine a data type of said first set of input values and said second set of input values; and
control said at least one function of said vehicle based on one of said determined data type or a personalization setting associated with said first user.

3. The device according to claim 2, wherein
said circuitry is further configured to determine said operating mode based on one of current location information of said vehicle, a motion status of said vehicle, or said determined data type, and
said operating mode corresponds to one of a home mode, an about-to-drive mode, an outside driving mode, an outside non-driving mode, a vehicle-health mode, or a user-critical health mode.

4. The device according to claim 1, wherein said at least one function includes at least one of an open operation of a vehicle door, a close operation of said vehicle door, control of vehicle ignition, control of vehicle speed, selection of a driving operation mode including an autonomous driving mode, set a destination of said vehicle, dynamic configuration of a personalization setting associated with said first user authenticated at said vehicle, adjustment of internal ambience of said vehicle, adjustment of a vehicle seat, adjustment of a position of a vehicle mirror, or synchronization of personal data collected from one of said plurality of wearable devices or an external device associated with said device.

5. The device according to claim 1, wherein said circuitry is further configured to prioritize, in an about-to-drive mode, said first user among said plurality of users to authenticate with said vehicle.

6. The device according to claim 5, wherein
said circuitry is further configured to communicate with said first wearable device at a time interval, and
said communication is based on a presence of said first user in said vehicle in an outside driving mode.

7. The device according to claim 6, wherein
said circuitry is further configured to communicate a theft alert to a communication device associated with said vehicle, and
said theft alert is communicated based on a lack of detection of said first user in said vehicle in said outside driving mode.

8. The device according to claim 5, wherein
said authentication is transferred from said first wearable device to said second wearable device in an outside non-driving mode to permit movement of said vehicle within a predetermined radial distance from said vehicle.

9. The device according to claim 1, wherein said circuitry is further configured to detect an abnormal medical condition of said first user based on said health data received from one of said plurality of wearable devices or a portable electronic device associated with said first user.

10. The device according to claim 9, wherein said circuitry is further configured to determine a level of said detected abnormal medical condition.

11. The device according to claim 10, wherein said circuitry is further configured to:
control vehicle speed;
transmit a health alert notification with current location information of said first user to at least one of a mobile device of a caregiver, a mobile device of a hospital, or a mobile device of an ambulance; and
generate guidance for said first user to reach said hospital based on at least one of said level of said detected abnormal medical condition, said operating mode, or said specific value.

12. The device according to claim 11, wherein said circuitry is further configured to receive a plurality of instructions from said caregiver for said control of said at least one function of said vehicle in an outside driving mode.

13. The device according to claim 10, wherein
said circuitry is further configured to drive said vehicle to a medical care center in a range of said vehicle, and
said vehicle is in at least one of an autonomous driving mode or an outside driving mode.

14. The device according to claim 1, wherein
said circuitry is further configured to:
detect said first user is outside said vehicle;
receive a current body temperature of said first user from said plurality of wearable devices based on said detection that said first user is outside said vehicle; and
control a temperature inside said vehicle based on said current body temperature of said first user, and
said operating mode is an outside non-driving mode.

15. The device according to claim 1, wherein
said circuitry is further configured to:
   detect said first user is inside said vehicle; and
   transmit a temperature change signal to an electronic control unit of said vehicle at a time interval based on said detection that said first user is inside said vehicle, and
   said operating mode is an outside driving mode.

16. The device according to claim 1, wherein said circuitry is further configured to:
   receive alcohol level associated with said first user from said first wearable device in a case where said operating mode is one of an about-to-drive mode or an outside driving mode, and
   control said at least one function of said vehicle based on said reception of said alcohol level.

17. The device according to claim 1, wherein
said circuitry is further configured to prioritize said first user of said plurality of users to authenticate with said vehicle, and
   said first user is prioritized based on a simultaneous detection of said plurality of users within said first proximity range of said device.

18. The device according to claim 3, wherein said circuitry is further configured to dynamically configure personalization settings associated with said first user when said operating mode is said about-to-drive mode.

19. A method for interaction management of a vehicle, said method comprising:
   receiving, by circuitry of a device in said vehicle, a first set of input values from a plurality of wearable devices, wherein
      said plurality of wearable devices is communicatively coupled to said device,
      said plurality of wearable devices comprises a first wearable device associated with a first user of a plurality of users, and
      said first set of input values includes a specific value associated with health data of said first user;
   receiving, by said circuitry, a second set of input values from at least one vehicle sensor in said vehicle;
   determining, by said circuitry, an operating mode of a plurality of operating modes of said device based on said first set of input values received from said plurality of wearable devices and said second set of input values received from said at least one vehicle sensor;
   determining, by said circuitry, that said specific value is within a first threshold and a second threshold;
   detecting, by said circuitry, said first wearable device is within a first proximity range of said device subsequent to said determination that said specific value is within said first threshold and said second threshold;
   authenticating, by said circuitry, said first user associated with said first wearable device based on:
      said specific value associated with said health data of said first user; and
      said detection that said first wearable device is within said first proximity range of said device;
   receiving, by said circuitry, a request from said first wearable device to transfer said authentication from said first wearable device to a second wearable device of said plurality of wearable devices, wherein
      said second wearable device is associated with a second user of said plurality of users, and
      said first wearable device is different from said second wearable device;
   transferring, by said circuitry, said authentication to said second wearable device from said first wearable device for a specific time period based on said request;
   detecting, by said circuitry, said second wearable device is in a second proximity range of said vehicle;
   recognizing, by said circuitry, enablement of an authentication transfer feature on said second wearable device based on said detection of said second wearable device in said second proximity range of said vehicle, wherein said authentication transfer feature indicates said transferred authentication; and
   controlling, by said circuitry, at least one function of said vehicle based on said recognition.

20. The method according to claim 19, further comprising determining, by said circuitry, a data type of said first set of input values and said second set of input values, wherein said controlling of said at least one function of said vehicle is further based on at least one of said data type or a personalization setting associated with said first user.

21. The method according to claim 20, further comprising determining said operating mode, by said circuitry, based on at least one of current location information of said vehicle, a motion status of said vehicle, or said data type, wherein said operating mode corresponds to one of a home mode, an about-to-drive mode, an outside driving mode, an outside non-driving mode, a vehicle-health mode, or a user-critical health mode.

22. A vehicle, comprising:
   a battery;
   an electronic control unit;
   a device, powered by said battery, configured to:
      control communication between a plurality of wearable devices,
         wherein said plurality of wearable devices comprises a first wearable device associated with a first user of a plurality of users and said electronic control unit; and
      receive a first set of input values from said plurality of wearable devices, wherein
         said plurality of wearable devices is communicatively coupled to said device, and
         said first set of input values includes a specific value associated with health data of said first user; and
   at least one vehicle sensor in said vehicle configured to communicate a second set of input values to said device,
      wherein said device is further configured to:
         determine an operating mode of a plurality of operating modes of said device based on said first set of input values received from said plurality of wearable devices and said second set of input values received from said at least one vehicle sensor in said vehicle;
         determine that said specific value is within a first threshold and a second threshold;
         detect said first wearable device is within a first proximity range of said device subsequent to said determination that said specific value is within said first threshold and said second threshold;
         authenticate said first user associated with said first wearable device based on:
            said specific value associated with said health data of said first user; and
            said detection that said first wearable device is within said first proximity range of said device;
         receive a request from said first wearable device to transfer said authentication from said first wearable device to a second wearable device of said plurality of wearable devices, wherein
    said second wearable device is associated with a second user of said plurality of users, and
    said first wearable device is different from said second wearable device;
transfer said authentication to said second wearable device from said first wearable device for a specific time period based on said request;
detect said second wearable device is in a second proximity range of said vehicle;
recognize enablement of an authentication transfer feature on said second wearable device based on said detection of said second wearable device in said second proximity range of said vehicle, wherein said authentication transfer feature indicates said transferred authentication; and
control at least one function of said vehicle based on said recognition.

* * * * *